(12) United States Patent
Hird et al.

(10) Patent No.: US 7,717,893 B2
(45) Date of Patent: May 18, 2010

(54) ABSORBENT ARTICLES COMPRISING A SLOW RECOVERY ELASTOMER

(75) Inventors: Bryn Hird, Colerain Township, OH (US); Robin Lynn McKiernan, Mason, OH (US); Edward Joseph Urankar, Mason, OH (US); Janet Neton, West Chester, OH (US); Mattias Schmidt, Idstein, OH (US); Joerg Mueller, Karben (DE)

(73) Assignee: The Procter & Gamble Company, Cincinnati, OH (US)

(*) Notice: Subject to any disclaimer, the term of this patent is extended or adjusted under 35 U.S.C. 154(b) by 225 days.

(21) Appl. No.: 11/144,508

(22) Filed: Jun. 3, 2005

(65) Prior Publication Data

US 2005/0273072 A1 Dec. 8, 2005

Related U.S. Application Data

(60) Provisional application No. 60/577,037, filed on Jun. 4, 2004.

(51) Int. Cl.
| | |
|---|---|
| *A61F 13/15* | (2006.01) |
| *A61F 13/20* | (2006.01) |
| *A01K 1/15* | (2006.01) |
| *D02G 3/00* | (2006.01) |
| *B32B 25/04* | (2006.01) |
| *B32B 25/12* | (2006.01) |
| *C08F 290/14* | (2006.01) |

(52) U.S. Cl. ............... 604/385.01; 604/358; 604/365; 604/372; 604/373; 604/385.23; 428/221; 428/364; 428/492; 525/50

(58) Field of Classification Search ............... 604/358, 604/385.1, 386, 387, 388, 389, 390, 391, 604/392, 393; 428/224, 903, 284, 364, 913; 525/97, 98, 99
See application file for complete search history.

(56) References Cited

U.S. PATENT DOCUMENTS

| | | |
|---|---|---|
| 636,558 A | 11/1899 | Reich |
| 3,086,242 A | 4/1963 | Cook et al. |
| 3,139,468 A | 6/1964 | Wheat |
| 3,370,630 A | 2/1968 | Gordon, et al. |

(Continued)

FOREIGN PATENT DOCUMENTS

CH 528285 2/1968

(Continued)

OTHER PUBLICATIONS http://en.wikipedia.org/wiki/Polypropylene.*

(Continued)

*Primary Examiner*—Leslie R Deak
*Assistant Examiner*—Adam Marcetich
(74) *Attorney, Agent, or Firm*—John G. Powell; Richard L. Alexander; Eric T. Addington

(57) ABSTRACT

An absorbent article comprising at least one topsheet; a liquid impervious backsheet joined with the topsheet; an absorbent core interposed between the topsheet and backsheet; and a slow recovery elastomer. The slow recovery elastomer exhibits a normalized unload force at 37° C. of greater than about 0.04N and at least about 20% post elongation strain at 22° C. after 15 seconds of recovery.

101 Claims, 6 Drawing Sheets

U.S. PATENT DOCUMENTS

| | | |
|---|---|---|
| 3,587,581 A | 6/1971 | Jones, Sr. |
| 3,592,946 A | 7/1971 | Griffith |
| 3,601,923 A | 8/1971 | Rosenberg |
| 3,639,917 A | 2/1972 | Althouse |
| 3,819,401 A | 6/1974 | Massengale et al. |
| 3,848,594 A | 11/1974 | Buell |
| 3,860,003 A | 1/1975 | Buell |
| 3,911,173 A | 10/1975 | Sprague, Jr. |
| 3,912,565 A | 10/1975 | Koch et al. |
| 3,929,135 A | 12/1975 | Thompson |
| RE28,688 E | 1/1976 | Cook |
| 4,054,616 A | 10/1977 | Miki et al. |
| 4,089,913 A | 5/1978 | Miki et al. |
| 4,116,842 A | 9/1978 | Meier |
| 4,122,134 A | 10/1978 | Miki et al. |
| 4,152,370 A | 5/1979 | Moczygemba |
| 4,169,336 A | 10/1979 | Kuhn |
| 4,248,981 A | 2/1981 | Milkovich et al. |
| 4,248,982 A | 2/1981 | Bi et al. |
| 4,248,984 A | 2/1981 | Bi et al. |
| 4,259,220 A | 3/1981 | Bunnelle et al. |
| 4,324,246 A | 4/1982 | Mullane et al. |
| 4,337,771 A | 7/1982 | Pieniak et al. |
| 4,342,314 A | 8/1982 | Radel et al. |
| 4,346,198 A | 8/1982 | Doak et al. |
| 4,381,781 A | 5/1983 | Sciaraffa et al. |
| 4,412,087 A | 10/1983 | Trepka |
| 4,418,180 A | 11/1983 | Heinz et al. |
| 4,450,026 A | 5/1984 | Pieniak et al. |
| 4,463,045 A | 7/1984 | Ahr et al. |
| 4,515,595 A | 5/1985 | Kievit et al. |
| 4,573,986 A | 3/1986 | Minetola et al. |
| 4,603,155 A | 7/1986 | Muramori et al. |
| 4,609,191 A | 9/1986 | Remme |
| 4,609,518 A | 9/1986 | Curro et al. |
| 4,610,678 A | 9/1986 | Weisman et al. |
| 4,629,643 A | 12/1986 | Curro et al. |
| 4,636,207 A | 1/1987 | Buell |
| 4,662,875 A | 5/1987 | Hirotsu et al. |
| 4,673,402 A | 6/1987 | Weisman et al. |
| 4,681,580 A | 7/1987 | Reising et al. |
| 4,695,278 A | 9/1987 | Lawson |
| 4,698,242 A | 10/1987 | Salerno |
| 4,699,622 A | 10/1987 | Toussant et al. |
| 4,699,941 A | 10/1987 | Salerno |
| 4,704,115 A | 11/1987 | Buell |
| 4,704,116 A | 11/1987 | Enloe |
| 4,704,434 A | 11/1987 | Kitchen et al. |
| 4,710,189 A | 12/1987 | Lash |
| 4,719,261 A | 1/1988 | Bunnelle et al. |
| 4,720,415 A | 1/1988 | Vander Wielen et al. |
| 4,761,198 A | 8/1988 | Salerno |
| 4,785,996 A | 11/1988 | Ziecker et al. |
| 4,787,897 A | 11/1988 | Torimae et al. |
| 4,795,454 A | 1/1989 | Dragoo |
| 4,801,485 A * | 1/1989 | Sallee et al. ................ 428/198 |
| 4,808,178 A | 2/1989 | Aziz et al. |
| 4,816,025 A | 3/1989 | Foreman |
| 4,816,094 A | 3/1989 | Pomplun et al. |
| 4,820,590 A | 4/1989 | Hodgson, Jr. et al. |
| 4,834,735 A | 5/1989 | Alemany et al. |
| 4,842,666 A | 6/1989 | Werenicz |
| 4,846,815 A | 7/1989 | Scripps |
| 4,846,827 A * | 7/1989 | Sallee et al. ........... 604/385.26 |
| 4,857,067 A | 8/1989 | Wood et al. |
| 4,874,255 A | 10/1989 | Ball et al. |
| 4,888,231 A | 12/1989 | Angstadt |
| 4,892,536 A | 1/1990 | Desmarais et al. |
| 4,894,060 A | 1/1990 | Nestegard |
| 4,900,317 A | 2/1990 | Buell |
| 4,909,803 A | 3/1990 | Aziz et al. |
| 4,938,753 A | 7/1990 | Van Gompel et al. |
| 4,939,208 A | 7/1990 | Lanza et al. |
| 4,940,464 A | 7/1990 | Van Gompel et al. |
| 4,946,527 A | 8/1990 | Battrell |
| 4,963,140 A | 10/1990 | Robertson et al. |
| 4,965,122 A | 10/1990 | Morman |
| 4,968,312 A | 11/1990 | Khan |
| 4,981,747 A | 1/1991 | Morman et al. |
| 4,987,194 A | 1/1991 | Maeda et al. |
| 4,988,344 A | 1/1991 | Reising et al. |
| 4,988,345 A | 1/1991 | Reising |
| 4,990,147 A | 2/1991 | Freeland |
| 5,006,394 A | 4/1991 | Baird |
| 5,026,364 A | 6/1991 | Robertson |
| 5,028,646 A | 7/1991 | Miller et al. |
| 5,036,978 A | 8/1991 | Frank et al. |
| 5,037,416 A | 8/1991 | Allen et al. |
| 5,047,484 A | 9/1991 | Tung |
| 5,049,591 A | 9/1991 | Hayashi et al. |
| 5,050,742 A * | 9/1991 | Muckenfuhs ................ 206/494 |
| 5,054,619 A | 10/1991 | Muckenfuhs |
| 5,062,840 A * | 11/1991 | Holt et al. .............. 604/385.19 |
| 5,085,654 A | 2/1992 | Buell |
| 5,089,558 A | 2/1992 | Hall et al. |
| 5,092,861 A | 3/1992 | Nomura et al. |
| 5,093,384 A | 3/1992 | Hayashi et al. |
| 5,098,776 A | 3/1992 | Kobayashi et al. |
| 5,114,781 A | 5/1992 | Morman |
| 5,116,662 A | 5/1992 | Morman |
| 5,118,762 A | 6/1992 | Chin |
| 5,135,786 A | 8/1992 | Hayashi et al. |
| 5,137,537 A | 8/1992 | Herron et al. |
| 5,139,832 A | 8/1992 | Hayashi et al. |
| 5,145,935 A | 9/1992 | Hayashi |
| 5,147,345 A | 9/1992 | Young et al. |
| 5,149,741 A | 9/1992 | Alper et al. |
| 5,151,092 A | 9/1992 | Buell et al. |
| 5,156,793 A | 10/1992 | Buell et al. |
| 5,156,911 A | 10/1992 | Stewart |
| 5,159,022 A | 10/1992 | Ikematu et al. |
| 5,167,897 A | 12/1992 | Weber et al. |
| 5,171,236 A | 12/1992 | Dreier et al. |
| 5,188,627 A | 2/1993 | Igaue et al. |
| 5,189,110 A | 2/1993 | Ikematu et al. |
| 5,192,301 A | 3/1993 | Kamiya et al. |
| 5,221,274 A | 6/1993 | Buell et al. |
| 5,226,992 A | 7/1993 | Morman |
| 5,234,999 A | 8/1993 | Tung et al. |
| 5,242,436 A | 9/1993 | Weil et al. |
| 5,246,433 A | 9/1993 | Hasse et al. |
| 5,256,736 A | 10/1993 | Trepka et al. |
| 5,260,345 A | 11/1993 | Desmarais et al. |
| 5,269,755 A | 12/1993 | Bodicky |
| 5,270,388 A | 12/1993 | Onishi et al. |
| 5,288,791 A * | 2/1994 | Collier et al. ................ 524/505 |
| 5,296,184 A | 3/1994 | Wu |
| 5,304,599 A * | 4/1994 | Himes ......................... 525/98 |
| 5,306,266 A | 4/1994 | Freeland |
| 5,336,545 A | 8/1994 | Morman |
| 5,342,338 A | 8/1994 | Roe |
| 5,344,691 A | 9/1994 | Hanschen et al. |
| 5,358,500 A | 10/1994 | Lavon et al. |
| 5,358,783 A | 10/1994 | Diehl et al. |
| 5,387,207 A | 2/1995 | Dyer et al. |
| 5,387,450 A | 2/1995 | Stewart |
| 5,397,316 A | 3/1995 | LaVon et al. |
| 5,397,318 A | 3/1995 | Dreier |
| 5,429,856 A | 7/1995 | Krueger et al. |
| 5,439,459 A | 8/1995 | Tanji et al. |
| 5,439,966 A | 8/1995 | Graham et al. |
| 5,445,140 A | 8/1995 | Tovey |
| 5,447,508 A | 9/1995 | Numano et al. |
| 5,468,237 A | 11/1995 | Miller et al. |

| | | |
|---|---|---|
| 5,468,428 A | 11/1995 | Hanschen et al. |
| 5,492,751 A | 2/1996 | Butt, Sr. et al. |
| 5,499,978 A | 3/1996 | Buell et al. |
| 5,506,300 A | 4/1996 | Ward et al. |
| 5,507,736 A | 4/1996 | Clear et al. |
| 5,514,121 A | 5/1996 | Roe et al. |
| 5,518,433 A | 5/1996 | Sneddon |
| 5,518,801 A | 5/1996 | Chappell et al. |
| 5,536,563 A * | 7/1996 | Shah et al. ............ 442/329 |
| 5,540,671 A | 7/1996 | Dreier |
| 5,540,976 A | 7/1996 | Shawver et al. |
| 5,545,690 A | 8/1996 | Trepka et al. |
| 5,554,142 A | 9/1996 | Dreier et al. |
| 5,554,145 A | 9/1996 | Roe et al. |
| 5,569,234 A | 10/1996 | Buell et al. |
| 5,571,096 A | 11/1996 | Dobrin et al. |
| 5,580,411 A | 12/1996 | Nease et al. |
| H1630 H | 1/1997 | Roe et al. |
| 5,591,152 A | 1/1997 | Buell et al. |
| 5,607,760 A | 3/1997 | Roe |
| 5,609,587 A | 3/1997 | Roe |
| 5,620,780 A | 4/1997 | Krueger et al. |
| 5,625,222 A | 4/1997 | Yoneda et al. |
| 5,634,913 A | 6/1997 | Stinger |
| 5,635,191 A | 6/1997 | Roe et al. |
| 5,641,562 A * | 6/1997 | Larson et al. ........... 442/394 |
| H1670 H | 7/1997 | Aziz et al. |
| 5,643,588 A | 7/1997 | Roe et al. |
| 5,648,167 A | 7/1997 | Peck |
| 5,653,703 A | 8/1997 | Roe et al. |
| 5,669,897 A | 9/1997 | Lavon et al. |
| 5,691,034 A | 11/1997 | Krueger et al. |
| 5,714,548 A | 2/1998 | Ma et al. |
| 5,719,226 A | 2/1998 | Kegley |
| H1732 H | 6/1998 | Johnson |
| 5,762,641 A | 6/1998 | Bewick-Sonntag et al. |
| 5,814,705 A | 9/1998 | Ward et al. |
| 5,830,203 A * | 11/1998 | Suzuki et al. ........ 604/385.19 |
| 5,853,864 A | 12/1998 | Bunnelle |
| 5,858,150 A | 1/1999 | Yarusso et al. |
| 5,865,823 A | 2/1999 | Curro |
| 5,889,118 A | 3/1999 | Delgado et al. |
| 5,897,545 A | 4/1999 | Kline et al. |
| 5,899,895 A | 5/1999 | Robles et al. |
| 5,910,546 A | 6/1999 | Trepka et al. |
| 5,916,206 A | 6/1999 | Otsubo et al. |
| 5,934,470 A | 8/1999 | Bauer et al. |
| 5,938,648 A | 8/1999 | Lavon et al. |
| 5,941,864 A | 8/1999 | Roe |
| 5,957,908 A | 9/1999 | Kline et al. |
| 5,968,025 A | 10/1999 | Roe et al. |
| 5,972,519 A | 10/1999 | Niessner et al. |
| 5,977,430 A | 11/1999 | Roe et al. |
| 5,997,520 A | 12/1999 | Ahr et al. |
| 6,004,306 A | 12/1999 | Robles et al. |
| 6,010,490 A | 1/2000 | Freeland et al. |
| 6,013,063 A | 1/2000 | Roe et al. |
| 6,025,071 A | 2/2000 | Cameron et al. |
| 6,031,053 A | 2/2000 | Knoll et al. |
| 6,063,838 A | 5/2000 | Patnode et al. |
| 6,103,814 A | 8/2000 | Vandrongelen et al. |
| 6,107,537 A | 8/2000 | Elder et al. |
| 6,120,487 A | 9/2000 | Ashton |
| 6,120,489 A | 9/2000 | Johnson et al. |
| 6,120,866 A | 9/2000 | Arakawa et al. |
| 6,140,433 A | 10/2000 | Zhang et al. |
| 6,149,637 A | 11/2000 | Allen et al. |
| 6,156,842 A | 12/2000 | Hoenig et al. |
| 6,168,584 B1 | 1/2001 | Allen et al. |
| 6,177,517 B1 | 1/2001 | Guntherberg et al. |
| 6,179,820 B1 | 1/2001 | Fernfors |
| 6,184,285 B1 | 2/2001 | Hatfield et al. |
| 6,187,696 B1 | 2/2001 | Lim et al. |
| 6,190,768 B1 | 2/2001 | Turley et al. |
| 6,193,701 B1 | 2/2001 | Van Gompel et al. |
| 6,194,073 B1 | 2/2001 | Li et al. |
| 6,197,889 B1 | 3/2001 | Knoll et al. |
| 6,211,272 B1 | 4/2001 | Shafer et al. |
| 6,235,847 B1 | 5/2001 | Hoshi et al. |
| 6,245,050 B1 | 6/2001 | Odorzynski et al. |
| 6,265,484 B1 | 7/2001 | Trepka et al. |
| 6,265,485 B1 | 7/2001 | Trepka et al. |
| 6,274,666 B1 | 8/2001 | Dougherty |
| 6,274,685 B2 | 8/2001 | Blok et al. |
| 6,288,149 B1 | 9/2001 | Kroll |
| 6,300,208 B1 | 10/2001 | Talwar et al. |
| 6,310,154 B1 | 10/2001 | Babcock et al. |
| 6,357,499 B1 | 3/2002 | Kralevich, Jr. et al. |
| 6,369,160 B1 | 4/2002 | Knoll et al. |
| 6,372,853 B1 | 4/2002 | Li et al. |
| 6,383,431 B1 | 5/2002 | Dobrin et al. |
| 6,410,129 B2 * | 6/2002 | Zhang et al. ............ 428/318.6 |
| 6,418,848 B1 | 7/2002 | Fujimoto et al. |
| 6,419,798 B1 | 7/2002 | Topolkaraev et al. |
| 6,423,807 B1 | 7/2002 | Oi et al. |
| 6,432,098 B1 | 8/2002 | Kline et al. |
| 6,444,755 B1 | 9/2002 | Deporter et al. |
| 6,455,627 B1 | 9/2002 | De Keyzer et al. |
| 6,465,557 B1 | 10/2002 | De Keyzer et al. |
| 6,476,288 B1 | 11/2002 | Vanrijswijck et al. |
| 6,482,191 B1 | 11/2002 | Roe et al. |
| 6,521,704 B1 | 2/2003 | Hubbard et al. |
| 6,531,544 B1 | 3/2003 | Vaughan et al. |
| 6,533,987 B2 | 3/2003 | Topolkaraev et al. |
| 6,547,915 B2 * | 4/2003 | Taylor et al. ............ 156/308.4 |
| 6,565,549 B1 | 5/2003 | Allen et al. |
| 6,571,704 B1 | 6/2003 | Fujimoto et al. |
| 6,579,940 B1 | 6/2003 | Dove |
| 6,592,995 B2 | 7/2003 | Topolkaraev et al. |
| 6,593,430 B1 | 7/2003 | Knoll et al. |
| 6,598,637 B2 | 7/2003 | Lechtenböhmer et al. |
| 6,617,016 B2 * | 9/2003 | Zhang et al. ............ 428/318.6 |
| 6,626,879 B1 | 9/2003 | Ashton et al. |
| 6,627,673 B2 | 9/2003 | Topolkaraev et al. |
| 6,635,041 B1 | 10/2003 | Popp et al. |
| 6,648,869 B1 | 11/2003 | Gillies et al. |
| 6,657,000 B1 | 12/2003 | De Keyzer et al. |
| 6,664,309 B2 | 12/2003 | Svenningsen et al. |
| 6,664,436 B2 | 12/2003 | Topolkaraev et al. |
| 6,673,857 B1 | 1/2004 | Knoll et al. |
| H2100 H | 4/2004 | Hansen et al. |
| 6,722,910 B2 | 4/2004 | Kajinuma |
| 6,746,433 B1 | 6/2004 | Shimoe et al. |
| 6,759,454 B2 | 7/2004 | Stephens et al. |
| 6,759,481 B2 | 7/2004 | Tong |
| 6,790,911 B2 | 9/2004 | Perevosnik et al. |
| 6,818,093 B1 | 11/2004 | Taal et al. |
| 6,827,806 B2 | 12/2004 | Uitenbroek et al. |
| 6,844,383 B2 | 1/2005 | Hoshi et al. |
| 6,887,916 B2 | 5/2005 | Zhou et al. |
| 6,933,421 B2 | 8/2005 | Topolkaraev et al. |
| 6,939,906 B2 | 9/2005 | Hoshi et al. |
| 6,946,172 B2 | 9/2005 | Munn et al. |
| 6,967,178 B2 | 11/2005 | Zhou et al. |
| 6,969,441 B2 | 11/2005 | Welch et al. |
| 6,978,486 B2 | 12/2005 | Zhou et al. |
| 7,015,155 B2 | 3/2006 | Zhou et al. |
| 7,056,411 B2 | 6/2006 | Desai et al. |
| 7,074,484 B2 | 7/2006 | Topolkaraev et al. |
| 7,087,287 B2 | 8/2006 | Curro et al. |
| 7,223,261 B2 | 5/2007 | Müeller et al. |
| 7,316,840 B2 | 1/2008 | Neculescu et al. |

| | | | | | | |
|---|---|---|---|---|---|---|
| 7,316,842 B2 | 1/2008 | Zhou et al. | | EP | 1013291 A1 | 6/2000 |
| 2001/0004689 A1 | 6/2001 | Otsubo | | EP | 1351815 | 2/2005 |
| 2002/0056384 A1 | 5/2002 | Fujimoto et al. | | EP | 1226018 | 10/2005 |
| 2002/0096072 A1 | 7/2002 | Fujimoto et al. | | GB | 2 297 473 A | 8/1995 |
| 2002/0115744 A1 | 8/2002 | Svenningsen et al. | | GB | 2 287 888 A | 10/1995 |
| 2002/0115772 A1 | 8/2002 | Topolkaraev et al. | | GB | 2 328 158 A | 2/1999 |
| 2002/0115977 A1 | 8/2002 | Topolkaraev et al. | | GB | 2 329 842 A | 4/1999 |
| 2002/0143313 A1 | 10/2002 | Tsuji et al. | | JP | 62241944 A | 10/1987 |
| 2002/0147273 A1 | 10/2002 | Patel et al. | | JP | 63238153 A | 10/1988 |
| 2002/0165516 A1 | 11/2002 | Datta et al. | | JP | 3160083 A | 7/1991 |
| 2003/0088228 A1 | 5/2003 | Desai et al. | | JP | 3160084 A | 7/1991 |
| 2003/0091807 A1 | 5/2003 | Desai et al. | | JP | 3239738 A | 10/1991 |
| 2003/0111166 A1 | 6/2003 | Uitenbroek et al. | | JP | 4153288 A | 5/1992 |
| 2003/0120240 A1 | 6/2003 | Buell et al. | | JP | 7157738 A | 6/1995 |
| 2003/0233082 A1 | 12/2003 | Kline et al. | | JP | 8060120 A | 3/1996 |
| 2004/0005832 A1 | 1/2004 | Neculescu et al. | | JP | 8060121 A | 3/1996 |
| 2004/0005834 A1 | 1/2004 | Zhou et al. | | JP | 8277382 A | 10/1996 |
| 2004/0005835 A1 | 1/2004 | Zhou et al. | | JP | 8281764 A | 10/1996 |
| 2004/0006324 A1 | 1/2004 | Zhou et al. | | JP | 9291265 A | 11/1997 |
| 2004/0013852 A1 | 1/2004 | Curro et al. | | JP | 9302319 A | 11/1997 |
| 2004/0092900 A1 | 5/2004 | Hoffman et al. | | JP | 2000-282006 | 5/1999 |
| 2004/0092902 A1 | 5/2004 | Hoffman et al. | | JP | 11279521 A | 10/1999 |
| 2004/0123938 A1 | 7/2004 | Zhou et al. | | JP | 2001040302 A | 2/2001 |
| 2004/0127881 A1 | 7/2004 | Stevens et al. | | JP | 2001279212 A | 10/2001 |
| 2004/0162536 A1 | 8/2004 | Becker et al. | | JP | 2001293789 A | 10/2001 |
| 2004/0162538 A1 | 8/2004 | Mueller et al. | | WO | WO 94/14395 | 7/1994 |
| 2004/0167486 A1 | 8/2004 | Busam et al. | | WO | WO 9414395 A1 | 7/1994 |
| 2004/0181200 A1 | 9/2004 | Desai et al. | | WO | WO 95/16746 | 6/1995 |
| 2004/0182499 A1 | 9/2004 | Collier, IV et al. | | WO | WO 9516746 A1 | 6/1995 |
| 2004/0193134 A1 | 9/2004 | Mueller et al. | | WO | WO 96/23823 | 1/1996 |
| 2004/0220304 A1* | 11/2004 | Smith et al. ............. 524/230 | | WO | WO 96/11236 A1 | 4/1996 |
| 2004/0222553 A1 | 11/2004 | Desai et al. | | WO | WO 98/08476 | 3/1998 |
| 2005/0095942 A1 | 5/2005 | Mueller | | WO | WO 99/13016 A1 | 3/1999 |
| 2005/0096416 A1 | 5/2005 | Zhou et al. | | WO | WO 00/12645 A1 | 3/2000 |
| 2005/0170729 A1 | 8/2005 | Stadelman et al. | | WO | WO 00/30581 A | 6/2000 |
| 2005/0171499 A1 | 8/2005 | Nigam et al. | | WO | WO 00/69834 | 11/2000 |
| 2005/0177123 A1 | 8/2005 | Catalan | | WO | WO 00/22061 A8 | 9/2001 |
| 2005/0211368 A1 | 9/2005 | McGuire | | WO | WO 01/87589 A | 11/2001 |
| 2005/0215963 A1 | 9/2005 | Autran et al. | | WO | WO 02/83786 A1 | 10/2002 |
| 2005/0215972 A1 | 9/2005 | Roe et al. | | WO | WO 03/047488 A | 6/2003 |
| 2005/0215973 A1 | 9/2005 | Roe et al. | | WO | WO 03/082571 A | 10/2003 |
| 2005/0256476 A1 | 11/2005 | Mirle et al. | | WO | WO 2006/074481 | 7/2006 |
| 2005/0273071 A1 | 12/2005 | McKiernan et al. | | | | |
| 2006/0003656 A1 | 1/2006 | Morman | | | | |
| 2006/0004342 A1 | 1/2006 | Sawyer et al. | | | | |
| 2006/0058765 A1 | 3/2006 | Mueller | | | | |
| 2006/0078042 A1 | 4/2006 | Lee | | | | |
| 2006/0083900 A1 | 4/2006 | Ashraf | | | | |
| 2006/0155255 A1 | 7/2006 | McKiernan et al. | | | | |
| 2006/0167434 A1 | 7/2006 | Ashton et al. | | | | |
| 2006/0264858 A1 | 11/2006 | Roe et al. | | | | |
| 2007/0037907 A9 | 2/2007 | Zhou et al. | | | | |
| 2007/0088307 A1 | 4/2007 | Arizti | | | | |
| 2007/0093771 A1 | 4/2007 | Arizti | | | | |
| 2007/0191806 A1 | 8/2007 | Mueller | | | | |
| 2007/0197993 A1 | 8/2007 | Arizti | | | | |
| 2007/0197994 A1 | 8/2007 | Arizti | | | | |
| 2008/0033388 A1 | 2/2008 | Mueller | | | | |
| 2008/0108963 A1 | 5/2008 | Ashton et al. | | | | |
| 2008/0195070 A1 | 8/2008 | Ponomarenko | | | | |

FOREIGN PATENT DOCUMENTS

| | | |
|---|---|---|
| DE | 1910911 | 3/1969 |
| EP | 119827 A2 | 9/1984 |
| EP | 0316671 | 11/1988 |
| EP | 0 433 951 B1 | 6/1991 |
| EP | 0 591 647 B1 | 4/1994 |
| EP | 0 597 331 A1 | 5/1994 |
| EP | 451919 B1 | 2/1995 |
| EP | 0 650 714 A1 | 5/1995 |
| EP | 0 703 068 B1 | 3/1996 |
| EP | 0 847 738 A1 | 6/1998 |

OTHER PUBLICATIONS http://en.wikipedia.org/wiki/PEX.*
U.S. Appl. No. 11/934,115, filed Nov. 2, 2007, Gregory Ashton et al.
PCT Search Report, mailed Jan. 20, 2006, 3 pages.
Polymer Handbook, Wiley Interscience, Section VII, $3_{rd}$ Edition, pp. 519-559, USA.
U.S. Appl. No. 11/145,353, filed Jun. 3, 2005, Office Action dated Dec. 11, 2007.
U.S. Appl. No. 11/145,353, filed Jun. 3, 2005, Office Action dated Jul. 30, 2008.
U.S. Appl. No. 11/144,497, filed Jun. 3, 2005, Office Action dated May 1, 2008.
U.S. Appl. No. 11/340,803, filed Jan. 26, 2006, Office Action dated Jun. 18, 2008.
Ziabicki, *Fundamentals of Fibre Formation*, John Wiley & Sons, New York (1976), Chapter 6.
J.H. Briston, *Plastic Films*, $2^{nd}$ Edition, Longman Inc., New York (1983), pp. 83-85.
I.M. Ward, *Mechanical Properties of Solid Polymers*, Wiley-Interscience, New York (1971), p. 278.
U.S. Appl. No. 11/145,353, filed Jun. 3, 2005, McKiernan et al., Office Action dated Feb. 10, 2009.

U.S. Appl. No. 11/145,353, filed Jun. 3, 2005, McKiernan et al., Office Action dated Jul. 30, 2008.
U.S. Appl. No. 11/145,353, filed Jun. 3, 2005, McKiernan et al., Office Action dated Dec. 11, 2007.
U.S. Appl. No. 11/340,803, filed Jan. 26, 2006, Ashton et al., Office Action dated Apr. 7, 2009.
U.S. Appl. No. 11/340,803, filed Jan. 26, 2006, Ashton et al., Office Action dated Dec. 16, 2008.
U.S. Appl. No. 11/340,803, filed Jan. 26, 2006, Ashton et al., Office Action dated Jun. 18, 2008.
U.S. Appl. No. 11/144,497, filed Jan. 26, 2006, McKiernan et al., Office Action dated Jan. 22, 2009.
U.S. Appl. No. 11/144,497, filed Jan. 26, 2006, McKiernan et al., Office Action dated May 1, 2008.

* cited by examiner

US 7,717,893 B2

ABSORBENT ARTICLES COMPRISING A SLOW RECOVERY ELASTOMER

CROSS REFERENCE TO RELATED APPLICATION

This application claims the benefit of U.S. Provisional Application No. 60/577,037, filed Jun. 4, 2004.

FIELD OF THE INVENTION

This invention is directed to absorbent articles such as diapers, training pants, adult incontinence articles, feminine hygiene articles, and the like comprising a slow recovery elastomer.

BACKGROUND OF THE INVENTION

Elastomeric compositions are well known in the art. Further, it has long been known in the field of disposable absorbent articles that it is desirable to construct absorptive devices, such as disposable diapers with fasteners, pull-on diapers, training pants, sanitary napkins, pantiliners, incontinence briefs, and the like, with elastic elements to improve the ease of motion and maintenance of a sustained fit. Furthermore, elastic elements allow the diaper to accommodate a range of different sized wearers. A diaper may have elastic elements in a number of its structures including the waist band, leg cuffs, side panels, elasticized topsheets, and backsheet. Diapers and other absorbent articles fitted with elastic elements, such as elasticized leg cuffs or elasticized waist bands, providing comfortable fit and leakage control are known in the art.

Many elastomeric compositions used to form elastic elements within current diapers are variants of synthetic rubber compositions. However, these elastomeric compositions tend to retract relatively rapidly when released from a stretched state. This complicates application of the absorbent article onto the wearer.

During application, a diaper generally may be stretched and elongated longitudinally and/or laterally from its initial substantially compacted and untensioned state. Upon release of the elongating tension, the diaper often contracts, constricts, and/or folds before it can be successfully applied to or adjusted on a wearer. In traditional taped diapers, the diaper generally is stretched longitudinally prior to application onto a wearer. However, if a continuous force is not maintained, the diaper will quickly retract. Generally, a caregiver needs to apply a continuous elongating force to the diaper while at the same time positioning the diaper onto the wearer and tending to the wearer who may uncooperative (e.g., crying, fussing, moving, resisting, etc.) in the diapering process. These multiple simultaneous requirements may lead to frustration for the caregiver. The multiple simultaneous requirements may result in the diaper being positioned improperly on the wearer.

Similarly, in pant-type articles, the waist region generally must be stretched and elongated to enlarge the waist opening from an initial substantially constricted and untensioned state. The waist often requires a continuous force to be applied during the application process, generally by a caregiver or wearer, to counteract the rapid retraction of the waist opening that would be experienced without a continuous application of the force. Leg openings in pants-type articles also tend to retract quickly and/or constrict the leg with force during application, increasing the difficulty of pulling the article up to the desired location on the wearer's upper thigh. Applying a continuous force to maintain an enlarged waist opening may be difficult for young children who lack the hand strength and dexterity to apply the continuous force while simultaneously pulling on the pant.

Recent diaper advancements have focused on the acceptance and storage of feces. In conventional diaper designs, feces remain between the diaper's topsheet and the wearer's skin. As a result, the wearer experiences excessive soiling, irritation, and the potential of leakage generally around the leg cuff. Advances in diaper design include the use of an apertured elasticized topsheet to isolate feces away from the wearer's skin thus preventing leakage and irritation. The apertured elasticized topsheet forms a void between the elasticized topsheet and the underlying diaper structure. The elastic within the elasticized topsheet aids in keeping the elasticized topsheet substantially in contact with the wearer's skin. Furthermore, the elastic aids in keeping the aperture positioned so as to receive fecal insult.

While elasticized topsheets are conceptually advantageous, diapers with elasticized topsheets comprising conventional elastomers are often difficult to apply. Application of the diaper requires a caregiver to stretch the diaper so that it is in a substantially planar position. Upon release, the elastic within elasticized topsheet contracts at a rate that makes it difficult for the caregiver to position the diaper correctly onto the wearer. This "snap-back" of the elasticized topsheet may increase the difficulty of applying the diaper to the wearer. If the diaper is difficult to apply, there may be a tendency for mispositioning the aperture. A mispositioned aperture may result in fecal deposit on the elasticized topsheet rather than through the aperture within the elasticized topsheet. Mispositioning of the aperture can destroy the benefit of isolating feces from the wearer's skin. Examples of diapers comprising an elasticized topsheet having an aperture have been disclosed in U.S. Pat. No. 4,892,536, issued to Des Marais et al. and U.S. Pat. No. 4,990,147 issued to Freeland.

Thus, there is a need for an absorbent product comprising elastomeric compositions that retract slowly upon being released from a stretched state, thus facilitating application and positioning of the product correctly onto the wearer.

SUMMARY OF THE INVENTION

In response to the deficiencies of prior diapers with elasticized topsheets, the present invention is directed to an absorbent article comprising a topsheet; a backsheet joined with the topsheet; an absorbent core interposed between the topsheet and backsheet; and a slow recovery elastomer joined to one or more article portions such as the topsheet, the backsheet, the core, an anal cuff, an elasticized topsheet, a fastening system, a leg cuff, an waist elastic feature, a side panel, a pocket, a spacer, and combinations thereof. The slow recovery elastomer may comprise about 20% to about 70%, by weight, of at least one elastomeric polymer. The slow recovery elastomer exhibits a normalized unload force at 37° C. of greater than about 0.04 N/mm² and a post elongation strain of at least about 50% after 15 seconds of recovery at 22° C.

The present invention also relates to an absorbent article comprising a topsheet; a backsheet joined with the topsheet; an absorbent core interposed between the topsheet and backsheet; and an elastic member comprising a slow recovery elastomer; wherein the slow recovery elastomer exhibits a normalized unload force at 37° C. of greater than about 0.04 N/mm² and a post elongation strain of at least about 50% after 15 seconds of recovery at 22° C.

The present invention also relates to an absorbent article comprising an elasticized topsheet; a secondary topsheet; a backsheet joined with the secondary topsheet; and an absorbent core interposed between the topsheet and secondary topsheet. The secondary topsheet may be positioned between the core and the elasticized topsheet. The elasticized topsheet has a slit opening through the elasticized topsheet. The slit opening allows entry to a void space between the elasticized topsheet and the secondary topsheet. The absorbent article also comprises a slow recovery elastomer joined to said elasticized topsheet and in proximity to the slit opening wherein the slow recovery elastomer exhibits a normalized unload force at 37° C. of greater than about 0.04 N/mm$^2$ and a post elongation strain of at least about 50% after 15 seconds of recovery at 22° C.

The present invention also relates to methods for applying the aforementioned absorbent articles.

DETAILED DESCRIPTION OF THE PRESENT INVENTIONS

Figure 1:
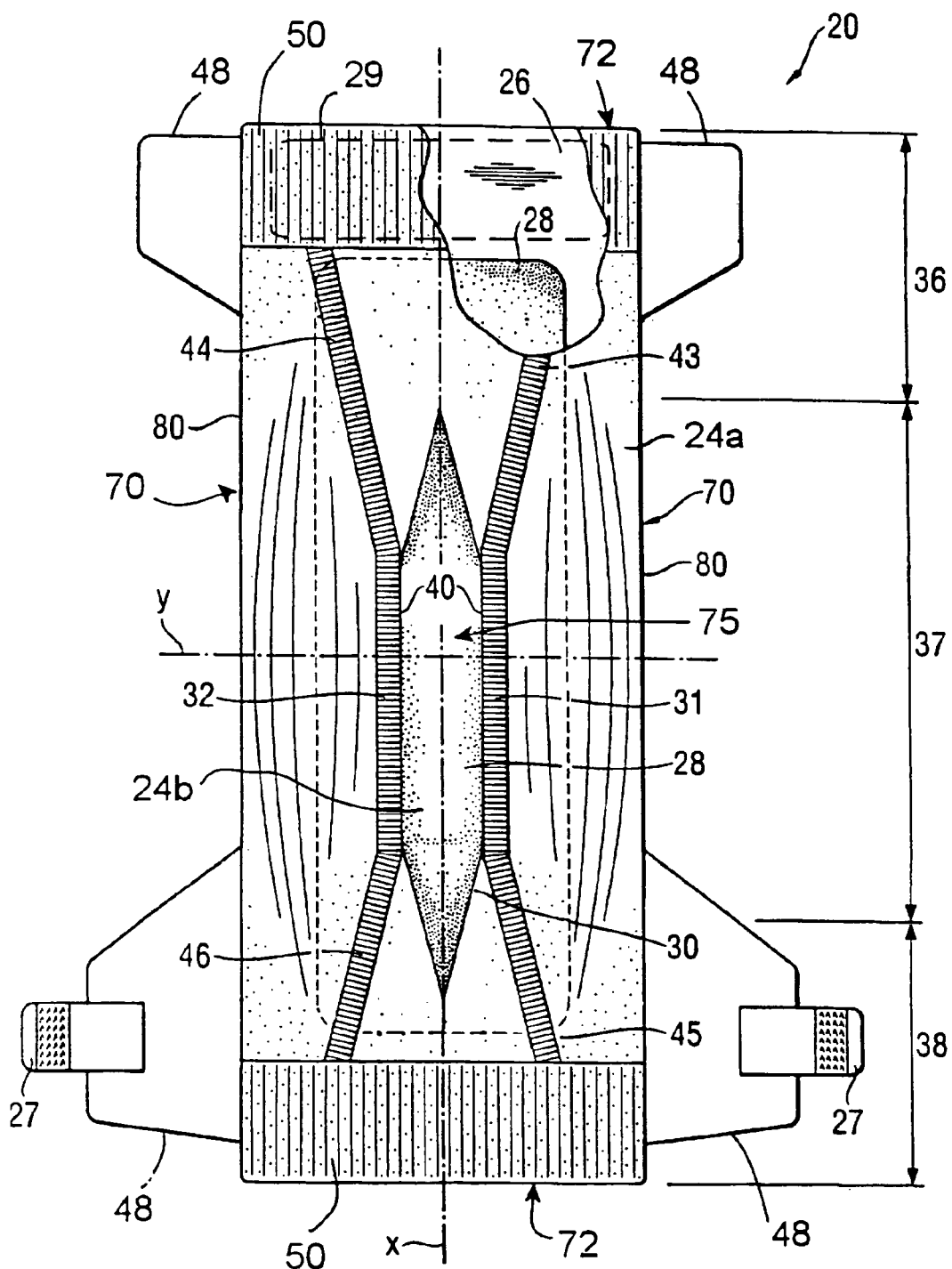
FIG. 1 is a top plan view of a diaper containing the slow recovery elastomer.

As used herein, the term "absorbent article" or "article" refers to a wearable device that absorbs and/or contains liquid and, more specifically, refers to a device that is placed against or in proximity to the body of the wearer to absorb and contain the various exudates discharged from the body. Suitable examples include diapers, training pants, pull-on garments, adult incontinence products and feminine care products such as sanitary napkins. Furthermore, "absorbent article" includes "disposable absorbent article" which is intended to be discarded and not laundered or otherwise restored after no more than ten uses, preferably after no more than five uses, and most preferably after a single use (although certain components may be recycled, reused, or composted).

As used herein, the term "elastic laminate" generally refers to a slow recovery elastomer which is attached to at least one substrate such as a polymeric film, a nonwoven, a woven, or a scrim. The elastomer may be attached to the substrate by any of a number of bonding methods known to those skilled in the art, including adhesive bonding, thermal bonding, pressure bonding, ultrasonic bonding, and the like.

As used herein, the term "diaper" refers to an absorbent article generally worn by infants and incontinent persons about the lower torso.

As used herein, the term "longitudinal" generally means a direction running parallel to the maximum linear dimension, typically the longitudinal axis, of the article and includes directions within 45° of the longitudinal direction.

As used herein, the term "length" of the article or component thereof generally refers to the size/distance of the maximum linear dimension, or typically to the size/distance of the longitudinal axis, or an article or part thereof.

As used herein, the terms "lateral" or "transverse" refer to a direction generally orthogonal to the longitudinal direction, e.g. in the same plan of the majority of the article and the longitudinal axis, and the transverse direction is parallel to the transverse axis.

As used herein, the term "width" of the article or of a component thereof refers to the size/distance of the dimension orthogonal to the longitudinal direction of the article or component thereof, e.g. orthogonal to the length of the article or component thereof, and typically it refers to the distance/size of the dimension parallel to the transverse axis of the article or component.

As used herein, the term "attached" encompasses configurations whereby an element is directly secured to another element by affixing the element directly to the other element.

As used herein, the term "joined" or "connected" encompasses configurations whereby an element is directly secured to another element by affixing the element directly to the other element and configurations whereby an element is indirectly secured to another element by affixing the element to intermediate member(s), which in turn are affixed to the other element.

As used herein, "relaxed" or "relaxed state" means the state that no forces are applied to the article (other than naturally occurring forces such as gravity), when the article is laid on a horizontal surface.

As used herein, the terms "extendibility" and "extensible", e.g. extendibility of the elastomer, mean that the width or length of the item in the relaxed position can be extended or increased.

As used herein, "elasticated" or "elasticized" means that the component comprises at least a portion made of elastic material.

As used herein, the terms "elastic", "elastomer" and "elastomeric" refer to a material which generally is able to extend to a strain of at least 50% without breaking or rupturing, and is able to recover substantially to its original dimensions after the deforming force has been removed.

As used herein, "along the longitudinal axis" means at least partially parallel to the longitudinal axis.

As used herein, the term "impermeable" generally refers to articles and/or elements that are not penetrative by fluid through the entire Z-directional thickness of the article under pressure of 0.14 lb/in$^2$ or less. Preferably, the impermeable article or element is not penetrative by fluid under pressures of 0.5 lb/in$^2$ or less. More preferably, the impermeable article or element is not penetrative by fluid under pressures of 1.0 lb/in$^2$ or less. The test method for determining impermeability conforms to Edana 120.1-18 or INDA IST 80.6, as described in copending U.S. patent application Ser. No. 10/844,182 filed May 12, 2004.

As used herein, the term "copolymer" refers to a polymer synthesized from two or more monomers with different chemical structures.

As used herein, the terms "temperature responsive" and "temperature responsiveness" refer to a slow recovery elastomer exhibiting less post elongation strain after a specified amount of time at higher temperatures than at lower temperatures.

The absorbent article of the present invention comprises a slow recovery elastomer. The slow recovery elastomer may be used within the absorbent article wherever an elastic material is desired. The slow recovery elastomer may be used discretely in the absorbent article. The slow recovery elastomer may be joined to another material or substrate (such as a polymeric film, a nonwoven, a woven, or a scrim) and used in the absorbent article. The slow recovery elastomer may be prepared from a composition comprising an elastomeric polymer, optionally at least one modifying resin, and optionally one or more additives. The slow recovery elastomer exhibits a normalized unload force at 37° C. of at least about 0.04 N/mm² as measured by the Two Cycle Hysteresis Test. The slow recovery elastomer exhibits a post elongation strain of 20% or greater after 15 seconds of recovery at 22° C. as measured by the Post Elongation Recovery Test.

A number of elastomeric polymers can be used to prepare the slow recovery elastomer with the requisite normalized unload force and post elongation strain. Elastomeric polymers include, but are not limited to, homopolymers (e.g., crosslinked poly(isoprene)), block copolymers, random copolymers, alternating copolymers, and graft copolymers. Suitable elastomeric polymers comprise styrenic block copolymers, natural and synthetic rubbers, polyisoprene, neoprene, polyurethanes, silicone rubbers, hydrocarbon elastomers, ionomers, and the like.

In one embodiment, the elastomeric polymer may be a block copolymer. A number of block copolymers may be used to prepare the slow recovery elastomer including multi-block, tapered block and star block copolymers. Generally, the block copolymers suitable for use in the slow recovery elastomer may exhibit both elastomeric and thermoplastic characteristics. In such block copolymers a hard block (or segment) may have a glass transition temperature (Tg) greater than about 25° C. or is crystalline or semicrystalline with a melting temperature (Tm) above about 25° C. Preferably, the hard block has a Tg greater than about 35° C. or is crystalline or semicrystalline with a Tm above about 35° C. The hard block portion is typically derived from vinyl monomers including vinyl arenes such as styrene and alpha-methyl-styrene or combinations thereof.

Glass transition temperatures referred to herein are determined by tensile dynamic mechanical analysis performed in the linear elastic region of the material at a frequency of 1 Hz using a temperature ramp method. Suitably, film samples with a uniform thickness of about 0.3 mm or less may be used with a temperature ramp rate of about 1° C./min or slower. The Tan δ peak temperature is taken as the Tg of the particular material or phase.

Crystalline melting temperatures referred to herein are determined by Differential Scanning Calorimetry using a temperature ramp rate of 10° C./min. The melting endotherm peak temperature is taken as the Tm of the particular crystalline region.

The block copolymers may comprise a soft block (or segment). The soft block generally exhibits a sufficiently low glass transition temperature and/or melting temperature so as not to form glassy or crystalline regions at the use temperature of the copolymer. In one embodiment, the use temperature may be between about room temperature (about 22° C.) and about body temperature (about 37° C.). However, other use temperatures are feasible and within the scope of this invention. Such soft blocks are generally physically incompatible with the hard blocks and form separate regions, domains, or phases.

The soft block portion may be a polymer derived from conjugated aliphatic diene monomers. Typically, the soft block monomers contain fewer than about 6 carbon atoms. Suitable diene monomers include butadiene, isoprene, and the like. Particularly preferred soft block polymers include poly(butadiene) and poly(isoprene). Furthermore, it is envisioned that the soft block may be modified to tailor the Tg of the soft block. For example, a random copolymer of isoprene and styrene or a graft of styrene onto poly(isoprene) may be used. In such cases, lower amounts of the modifying resin may be used.

Suitable block copolymers for use in this invention may comprise at least one hard block (A) and at least one soft block (B). The block copolymers may have multiple blocks. In a preferred embodiment, the block copolymer may be an A-B-A triblock copolymer, an A-B-A-B tetrablock copolymer, or an A-B-A-B-A pentablock copolymer. Also, useful herein are triblock copolymers having endblocks A and A', wherein A and A' may be derived from different vinyl compounds. Also, useful in the present invention are block copolymers having more than one hard block and/or more than one soft block, wherein each hard block may be derived from the same or different monomers and each soft block may be derived from the same or different monomers.

It should be noted that where the copolymer contains residual olefinic double bonds, the copolymer may be partially or fully hydrogenated if desired. Saturation may often yield beneficial effects in the elastomeric properties of the copolymer.

The elastomeric polymer may be used in the slow recovery elastomer in an effective amount so as to achieve the desired normalized unload forces and post elongation strains. The slow recovery elastomer generally may comprise from about 20% to about 70%, preferably about 30% to about 65%, and most preferably about 45% to about 60% of the elastomeric polymer.

Preferred elastomeric polymers include styrene-olefin-styrene triblock copolymers such as styrene-butadiene-styrene (S-B-S), styrene-ethylene/butylene-styrene (S-EB-S), styrene-ethylene/propylene-styrene (S-EP-S), styrene-isoprene-styrene (S-I-S), hydrogenated polystyrene-isoprene/butadiene-styrene (S-EEP-S), and mixtures thereof. The block copolymers may be employed alone or in a blend of block copolymers.

Particularly preferred block copolymers include styrene-butadiene-styrene (S-B-S) and styrene-isoprene-styrene (S-I-S) block copolymers. Such linear block copolymers of styrene-butadiene-styrene (S-B-S) and styrene-isoprene-styrene (S-I-S) are commercially available under the trade designation Vector from Dexco Polymers L. P., Houston, Tex., and under the trade designation Kraton from Kraton Polymers, Houston, Tex.

Various modifying resins may be used in this slow recovery elastomer. Suitable modifying resins should preferably associate or phase mix with the soft blocks of the elastomeric polymer. Modifying resins should have a sufficiently high molecular weight average such that the glass transition temperature of the soft block is increased resulting in an increase of post elongation strain at 22° C. after 15 seconds of recovery. While not intending to be bound by this theory, it is believed that the modifying resins raise the Tg of the soft phase to the point where molecular relaxation at the in-use temperature is slowed. This is evidenced by a relatively high post elongation strain.

The slow recovery elastomer may comprise the modifying resin in amounts from about 0% to about 60% by weight. Preferably, the composition comprises from about 20% to about 55% and even more preferably from about 35% to about 45% of the modifying resin.

Suitable modifying resins useful herein may have glass transition temperatures ranging from about 60° C. to about 180° C., more preferably from about 70° C. to about 150° C., and more preferably from about 90° C. to about 130° C.

Suitable modifying resins useful herein should preferably be soft block associating. A solubility parameter is useful in determining whether the modifying resin will phase mix with the soft block of the block copolymer. Generally, modifying resins are selected so that the solubility parameter of the modifying resin is similar to the solubility parameter of the soft block phase. Since common soft block phases have solubility parameters from about 7.0 $(cal/cm^3)^{1/2}$ to about 9.0 $(cal/cm^3)^{1/2}$, the modifying resins should have similar solubility parameters. For example in the case where the solubility parameter of the soft block phase is about 8 $(cal/cm^3)^{1/2}$, the solubility parameter of the modifying resin should be from about 7.5 $(cal/cm^3)^{1/2}$ to about 8.5 $(cal/cm^3)^{1/2}$. The solubility parameters of the modifying resins may also approximate the solubility of the hard block. However, as long as phase mixing of the modifying resin with the soft block exists, hard block phase mixing should not be read as limiting. A list of solubility parameters for common polymers or resins, along with methods for determining or approximating the solubility parameters can be found in the Polymer Handbook, Third Edition; Wiley Interscience; Section VII pages 519-559.

Modifying resins useful herein include, but are not limited to, unhydrogenated C5 hydrocarbon resins or C9 hydrocarbon resins, partially and fully hydrogenated C5 hydrocarbon resins or C9 hydrocarbon resins; cycloaliphatic resins; terpene resins; polystyrene and styrene oligomers; poly(t-butyl-styrene) or oligomers thereof; rosin and rosin derivatives; coumarone indenes; polycyclopentadiene and oligomers thereof; polymethylstyrene or oligomers thereof; phenolic resins; indene polymers, oligomers and copolymers; acrylate and methacrylate oligomers, polymers, or copolymers; derivatives thereof; and combinations thereof. Preferably, the resin is selected from the group consisting of the oligomers, polymers and/or copolymers derived from: t-butylstyrene, cyclopentadiene, iso-bornyl methacrylate, methyl methacrylate, isobutyl methacrylate, indene, coumarone, vinylcyclohexane, methylstyrene, and 3,3,5-trimethylcyclohexyl methacrylate. Preferred modifying resins also include alicyclic terpenes, hydrocarbon resins, cycloaliphatic resins, poly-beta-pinene, terpene phenolic resins, and combinations thereof. "C5 hydrocarbon resins" and "C9 hydrocarbon resins" are disclosed in U.S. Pat. No. 6,310,154.

In general, a variety of additives may be employed to yield a slow recovery elastomer with more favorable characteristics. For example, stabilizers, antioxidants, and bacteriostats may be employed to prevent thermal, oxidative, and biochemical degradation of the slow recovery elastomer. Generally, the additive or additives may account for about 0.01% to about 60% of the total weight of the slow recovery elastomer. In other embodiments, the composition comprises from about 0.01% to about 25%. In other suitable embodiments, the composition comprises from about 0.01% to about 10% by weight, of additives.

Various stabilizers and antioxidants are well known in the art and include high molecular weight hindered phenols (i.e., phenolic compounds with sterically bulky radicals in proximity to the hydroxyl group), multifunctional phenols (i.e., phenolic compounds with sulfur and phosphorous containing groups), phosphates such as tris-(p-nonylphenyl)-phosphite, hindered amines, and combinations thereof. Representative hindered phenols include t-butylhydroxyquinone; 1,3,5-trimethyl-2,4,6-tris(3-5-di-tert-butyl-4-hydroxybenzyl)benzene; pentaerythritol tetrakis-3(3,5-di-tert-butyl-4-hydroxyphenyl)propionate; n-octadecyl-3(3,5-ditert-butyl-4-hydroxyphenyl)propionate; 4,4'-methylenebis(4-methyl-6-tert butylphenol); 4,4'-thiobis(6-tert-butyl-o-cresol); 2,6-di-tert-butylphenol; 6-(4-hydroxyphenoxy)-2,4-bis(n-ocytlthio)-1,3,5-triazine; 2,4,6-tris(4-hydroxy-3,5-di-tert-butyl-phenoxy)-1,3,5-triazine; di-n-octadecyl-3,5-di-tert-butyl-4-ydroxybenzylphosphonate; 2-(n-octylthio)ethyl-3,5-di-tert-butyl-4-hydroxybenzoate; and sorbitol hexa-(3,3,5-di-tert-butyl-4-hydroxy-phenyl)propionate. Proprietary commercial stabilizers and/or antioxidants are avalaible under a number of trade names including a variety of Wingstay®, Tinuvin® and Irganox® products.

Various bacteriostats are known in the art and may be included as additives within the slow recovery elastomer. Examples of suitable bacteriostats include benzoates, phenols, aldehydes, halogen containing compounds, nitrogen compounds, and metal-containing compounds such as mercurials, zinc compounds and tin compounds. A representative bacteriostat is 2,4,4'-trichloro-2'-hydroxy-diphenyl-ether which is available under the trade designation Irgasan Pa. from Ciba Specialty Chemical Corporation, Tarrytown, N.Y.

Other optional additives include thermoplastic polymers or thermoplastic polymer compositions which preferentially associate with the hard blocks or segments of the block copolymers. Without intending to be bound by theory, it is believed that these thermoplastic polymers become incorporated into the entangled three-dimensional network structure of the hard phase. This entangled network structure can provide improved tensile, elastic and stress relaxation properties of the elastomeric composition. Where the elastomeric polymer comprises a styrenic block copolymer, thermoplastic polymer additives such as polyphenylene oxide and vinylarene polymers derived from monomers including styrene, alpha-methyl styrene, para-methyl styrene, other alkyl styrene derivatives, vinyl toluene, and mixtures thereof, are useful in the present invention because they are generally considered to be chemically compatible with the styrenic hard blocks of the block copolymer.

Various viscosity modifiers, processing aids, slip agents or anti-block agents can be employed as additives to yield a slow recovery elastomer with, for example, improved handling characteristics or surface characteristics. Processing aids include processing oils, which are well known in the art and include synthetic and natural oils, naphthenic oils, paraffinic oils, olefin oligomers and low molecular weight polymers, vegetable oils, animal oils, and derivatives of such including hydrogenated versions. Processing oils also may incorporate combinations of such oils. A particularly preferred processing oil is mineral oil. Viscosity modifiers are also well known in the art. For example, petroleum derived waxes can be used to reduce the viscosity of the slow recovery elastomer in thermal processing. Suitable waxes include low number-average molecular weight (e.g., 600-6000) polyethylene; petroleum waxes such as paraffin wax and microcrystalline wax; atactic polypropylene; synthetic waxes made by polymerizing carbon monoxide and hydrogen such as Fischer-Tropsch wax; and polyolefin waxes.

Various colorants and fillers are known in the art and may be included as additives within the slow recovery elastomer. Colorants can include dyes and pigments such as titanium dioxide. Fillers may include such materials as talc and clay. Other additives may include dyes, UV absorbers, odor control agents, perfumes, fillers, dessicants, and the like.

The slow recovery elastomers of the present invention exhibit unique elastic and recovery characteristics. The slow recovery elastomer exhibits a normalized unload force of greater than about 0.04 $N/mm^2$ at 37° C. as measured by the Two Cycle Hysteresis Test. Normalized unload forces of less than about 0.04 $N/mm^2$ at 37° C. are believed to be insufficient for use as an elastomer within absorbent articles. Materials having normalized unload forces less than 0.04 $N/mm^2$ at 37° C. are unable to keep an absorbent article in snug, close contact to the wearer's skin. Preferably, the slow recovery elastomer exhibits a normalized unload force of greater than about 0.08 N/mm$^2$ at 37° C., and, most preferably, exhibits a normalized unload force of greater than about 0.12 N/mm$^2$ at 37° C.

Traditional elastomers (i.e., those commonly used in disposable absorbent articles such as Vector 4211 from Dexco Polymers L. P., Houston, Tex.) exhibit minimal post elongation strain at 22° C. after 15 seconds of recovery. Qualitatively, traditional elastomers exhibit "snap back" (i.e., the elastomer contracts relatively quickly after being released from a stretched state). In the case of a diaper comprising an elasticized topsheet with a conventional elastomer, upon stretching and release of the diaper, the elastomer contracts relatively quickly, causing the diaper to fold, thus making it difficult to position and apply the diaper successfully. In contrast, the slow recovery elastomers of the current invention exhibit at least about 20% post elongation strain at 22° C. after 15 seconds of recovery, as measured by the Post Elongation Recovery Test. In other embodiments, the slow recovery elastomer exhibits at least about 50% post elongation strain after 15 seconds of recovery at 22° C. In other suitable embodiments, at 22° C. the slow recovery elastomer exhibits a post elongation strain from about 75% to about 150% after 15 seconds of recovery. However, post elongation strain after 15 seconds of recovery may exceed about 170% at 22° C.

Furthermore, the slow recovery elastomers of the present invention may exhibit a specified post elongation strain at 22° C. after 30 seconds, 60 seconds, or three minutes of recovery. In certain embodiments, the slow recovery elastomer may exhibit at least about a 70% post elongation strain after 30 seconds of recovery at 22° C. In other embodiments, the slow recovery elastomer may exhibit at least about a 40% post elongation strain after 60 seconds of recovery at 22° C.

The slow recovery elastomer may exhibit temperature responsiveness. In one embodiment, a temperature responsive slow recovery elastomer may exhibit a post elongation strain after 15 seconds at 32° C. that is at least 35% less than the post elongation strain after 15 seconds at 22° C. Preferably, at least a 50% reduction in post elongation strain is exhibited. Most preferably, at least a 75% reduction in post elongation strain is exhibited. It is believed that a slow recovery elastomer exhibiting temperature responsiveness may further facilitate diaper application. When the diaper is applied at about room temperature (e.g., approximately 22° C.), the slow recovery elastomer exhibits a relatively high degree of post elongation strain for a prescribed period of time. Upon application of the diaper, the slow recovery elastomer will rise in temperature because of the close proximity of the wearer's skin. As the temperature of the slow recovery elastomer increases and nears body temperature (e.g., approximately 32° C.), the reduced post elongation strain is exhibited. Temperature responsiveness allows for application of the diaper without "snap-back" while providing for increased recovery after application.

The slow recovery elastomer of the present invention may exist in a variety of forms. The slow recovery elastomer forms include, but are not limited to films, bands, strands, individualized fibers, or combinations thereof. Furthermore, the slow recovery elastomer may take any of the previous forms and be further combined with a traditional elastic not exhibiting the unique rate of recovery of the present invention (i.e., an elastic not exhibiting at least about 50% post elongation strain after 15 seconds of recovery at 22° C.). The slow recovery elastomer may be utilized in a variety of articles. However, the composition has particular benefit within absorbent articles, particularly disposable absorbent articles such as diapers and the like. The slow recovery elastomer may be used in place of or in addition to traditional elastomers commonly present in absorbent articles. The slow recovery elastomer may be used discretely or be may be joined to another material or substrate (such as a polymeric film, a nonwoven, a woven, or a scrim).

In the embodiment that follows, the absorbent article is in the form of a diaper 20. The elastomeric laminate of the present invention may be used in said embodiment wherever an elastic material is desired. FIG. 1 illustrates a diaper 20 in a top plan view, stretched, and in a substantially planar state. The surface of the diaper 20 that is positioned proximate to the wearer (i.e., wearer-facing surface) is shown. Portions of the diaper 20 have been cut away to more clearly show the underlying structure. One end portion of the diaper 20 may be configured as a first waist region 36 of the diaper 20. The opposite end portion may be configured as a second waist region 38 of the diaper 20. An intermediate portion of the diaper 20 may be configured as a crotch region 37 that extends longitudinally between the first and second waist regions 36 and 38. The crotch region 37 is that portion of the diaper 20 which, when the diaper 20 is worn, is generally positioned between the legs of the wearer. The waist regions 36 and 38 generally may comprise those waist portions of the diaper 20 which, when worn, encircle the waist of the wearer. The waist regions 36 and 38 may include elements which can gather about the waist of the wearer to provide improved fit and containment, or which typically can gather around the waist and can be fastened around the waist by use of a fastening system, such as tabs 27, which are fastened to landing zones 29.

The diaper 20 may comprise two longitudinal edges 70 and two lateral edges 72. The diaper 20 may also have a longitudinal axis designated as line x. The diaper may also have a lateral axis designated as line y.

The diaper 20 may comprise at least one topsheet (FIG. 1 shows two tops sheets designated 24a and 24b) that may be partially, fully, or not elasticated; a backsheet 26; and an absorbent core 28 interposed between the topsheet 24b and the backsheet 26. The diaper may also include side panels 48, a fastening system which may include fastening tabs 27 that can be secured to a landing zone 29, one or more pairs of leg cuffs 80, and/or a waist feature 50.

The diaper 20 may comprise more than one topsheet. In FIG. 1, the diaper exhibits two topsheets, an elasticized topsheet 24a and a secondary topsheet 24b. The secondary topsheet 24b may extend the width of the diaper 20 and may be positioned adjacent to the wearer-facing surface of the absorbent core 28. The secondary topsheet 24b may be used so that fecal insult will not adversely associate with the absorbent core 28. Generally in a diaper comprising two topsheets, the secondary topsheet 24b is the topsheet proximate to the garment-facing surface of the diaper 20 whereas the elasticized topsheet 24a is proximate to the wearer-facing surface. The secondary topsheet 24b may be joined to the core 28 and/or to the backsheet 26 by any attachment means known in the art. Suitable attachment means for joining the topsheets 24a and 24b are the same as those means, as described below, for joining the backsheet 26 to other elements of the diaper 20. In one embodiment of the present invention, the topsheets 24a and 24b and the backsheet 26 are joined along their respective longitudinal edge 70 and lateral edges 72. The elasticized topsheet 24a and the secondary topsheet 24b may be joined along one or more of their longitudinal edges 70 or lateral edges 72 and not along a substantial portion of their contacting planar faces. In certain embodiments, the secondary topsheet 24b is not attached to the core 28.

The secondary topsheet 24b may be liquid pervious, permitting liquids to readily penetrate through its thickness. The elasticized topsheet 24a is preferably compliant, soft-feeling, and non-irritating to the wearer's skin. The elasticized topsheet 24a may be hydrophobic in order to isolate liquids contained in the absorbent core 28 from the wearer's skin.

Suitable topsheets may be manufactured from a wide range of materials, such as porous foams, reticulated foams, apertured plastic films, or woven or nonwoven materials of natural fibers (e.g., wood or cotton fibers), synthetic fibers (e.g., polyester or polypropylene fibers), or a combination of natural and synthetic fibers. If the topsheets include fibers, the fibers may be spunbond, carded, wet-laid, meltblown, hydroentangled, or otherwise processed as is known in the art. One suitable secondary topsheet 24b comprising a web of hydrophilically treated spunbond polypropylene is available from BBA Fiberweb, Old Hickory, Tenn., under the designation P10 or 055SLPI09E. Suitable formed film topsheets are described in U.S. Pat. Nos. 3,929,135; 4,324,246; 4,342,314; 4,463,045; and 5,006,394. Other suitable conventional topsheets 24b may be made in accordance with U.S. Pat. Nos. 4,609,518 and 4,629,643. Exemplary formed films include "DRI-WEAVE" and "CLIFF-T" both from Tredegar Corporation, Richmond, Va.

In certain embodiments, at least a portion of the secondary topsheet 24b and the elasticized topsheet 24a may comprise a hydrophobic material or may be treated to be hydrophobic in order to isolate the wearer's skin from liquids contained in the absorbent core 28. Hydrophobicity may be achieved by eliminating the hydrophilizing treatment step from the production process and/or applying a hydrophobic treatment to the topsheets 24a and 24b, such as a fluoryl, paraffin, or silicone-based compound like Repellan ZN by Cognis Corporation, a hydrophobic surface coating as described in copending U.S. Provisional Application No. 60/543,785, which was filed Feb. 11, 2004, or a hydrophobic lotion composition, as described below. If the secondary topsheet 24b is made of a hydrophobic material, preferably at least a portion of its upper surface is treated to be hydrophilic so that liquids will transfer through the topsheet more rapidly. The secondary topsheet 24b can be rendered hydrophilic by treating it with a surfactant or by incorporating a surfactant into the topsheet. Suitable methods for treating the secondary topsheet 24b with a surfactant include spraying the material with the surfactant and/or immersing the material into the surfactant. A more detailed discussion of such a treatment and hydrophilicity is contained in U.S. Pat. Nos. 4,988,344 and 4,988,345. A more detailed discussion of some suitable methods for incorporating a surfactant in the topsheet can be found in U.S. Statutory Invention Registration No. H1670 published on Jul. 1, 1997 to Aziz et al. Alternatively, the secondary topsheet 24b may include an apertured web or film which is hydrophobic. In such embodiments, it is preferred that the apertures be large enough to allow the penetration of aqueous fluids like urine without significant resistance.

Any portion of the topsheets 24a and 24b, with preference to the elasticized topsheet 24a alone, may be coated with a lotion as is known in the art. Examples of suitable lotions include those described in U.S. Pat. Nos. 5,607,760; 5,609,587; 5,635,191; 5,643,588; and 5,968,025. The lotion may function alone or in combination with another agent as the hydrophobizing treatment described above. The topsheets may also include or be treated with antibacterial agents, such as disclosed in U.S. Statutory Invention Registration No. H1732 published on Jun. 2, 1998 to Johnson. Further, the topsheets 24a and 24b, the backsheet 26, or any portion of the topsheet or backsheet may be embossed and/or matte finished to provide a more cloth like appearance.

The diaper 20 may comprise a slit opening 30 through the elasticized topsheet 24a. The slit opening 30 may be located so that fecal exudates pass through the slit opening 30 and into a void space 75 formed between the elasticized topsheet 24a and the secondary topsheet 24b. In other embodiments without a secondary topsheet 24b, the void space 75 may be formed between the elasticized topsheet 24a and the absorbent core 28 and/or other underlying layers such as sub layers, acquisition layers and the like. The void space 75 entraps or encapsulates bodily waste. It is also contemplated that the void space 75 may be formed between two elements of the diaper 20, including but not limited to a topsheet (either a conventional or elasticized topsheet) and the backsheet 26, the acquisition layer and the core 28, the core 28 and the backsheet 26, etc.

The slit opening 30 may be shaped to allow passage of bodily waste. An example of a suitable shaped slit opening 30 is a hexagonal shaped slit opening 30 as shown in FIG. 1. However, it will be apparent to one of skill in the art that other shapes and sizes of the slit opening 30 are feasible.

The elasticized topsheet 24a may comprise an elastic member 31, 32. The elastic member 31, 32 may be located along at least a portion of the longitudinal edges 40 of the slit opening 30. The longitudinal edge 40 of the slit opening may be held against the wearer's skin allowing the feces to penetrate the slit opening 30 without deflection, via only the elastic forces supplied by the elastic member 31, 32, or optionally by use of a body adhering adhesive. The elastic member 31, 32 may assist in maintaining the elasticized topsheet 24a in close contact to the wearer's skin. The elastic member 31, 32 also may assist in maintaining the position of the slit opening 30 along a gluteal groove, including a perianal region.

The elastic member 31, 32 may be the slow recovery elastomer of the present invention in the form of a film, band, stand, scrim, or any other like form that can be joined to the elasticized topsheet 24a. The elastic member 31, 32 may comprise other traditional "fast" elastic materials including synthetic rubber such as supplied by Fulflex International, Ireland; polyurethane such as Lycra® available from Invista Inc., Wilmington, Del.; or a VFE material available from Tredegar Corporation, Richmond, Va. The slow recovery elastomer may be bonded to the elasticized topsheet 24a by any method well known in the art including heat bonding and the use of adhesives (e.g., HL-1620 available by H. B. Fuller Company of St. Paul, Minn.). The elastic laminate 31, 32 may be positioned along the longitudinal edges 40 of the slit opening 30. The elastic laminate 31, 32 may extend from the slit opening 30 in the direction of the waist regions, preferably in an X-shape, with a front elastic laminate 43, 44 and/or a back elastic laminate 45, 46. The elastic laminate may be attached to a waistband, if present.

The elastic member 31, 32 may be an elastic laminate that is formed and attached to the elasticized topsheet 24a. Elastic laminate formation is well known in the art. In one method for creating an elastic laminate, elastic stands, bands, films, or the like are attached to a substrate while in a stretched configuration. After attachment, the elastic strands are allowed to relax thereby gathering the substrate and creating an elastic laminate. In an alternative method, elastic strands or a film can be attached to one or more substrates in either a relaxed configuration or partially stretched configuration. The resulting laminate can be made stretchable (or more stretchable in the case of partially stretched strands or film) by subjecting the laminate to an elongation process which elongates the substrate permanently, but the elastic stands or layer only temporarily. Such processes are known in the art as "zero strain" elastic laminate formation, and the elongation of such laminates may be accomplished with suitable means such as rollers, engaging teeth, or the like. Examples of zero strain activation processing and formations of resulting elastic laminates are described in U.S. Pat. No. 5,167,897 issued to Weber et al. and U.S. Pat. No. 5,156,793 issued to Buell et al. Other methods for elastic laminate formation are conventional and within the scope of this description.

Figure 2:
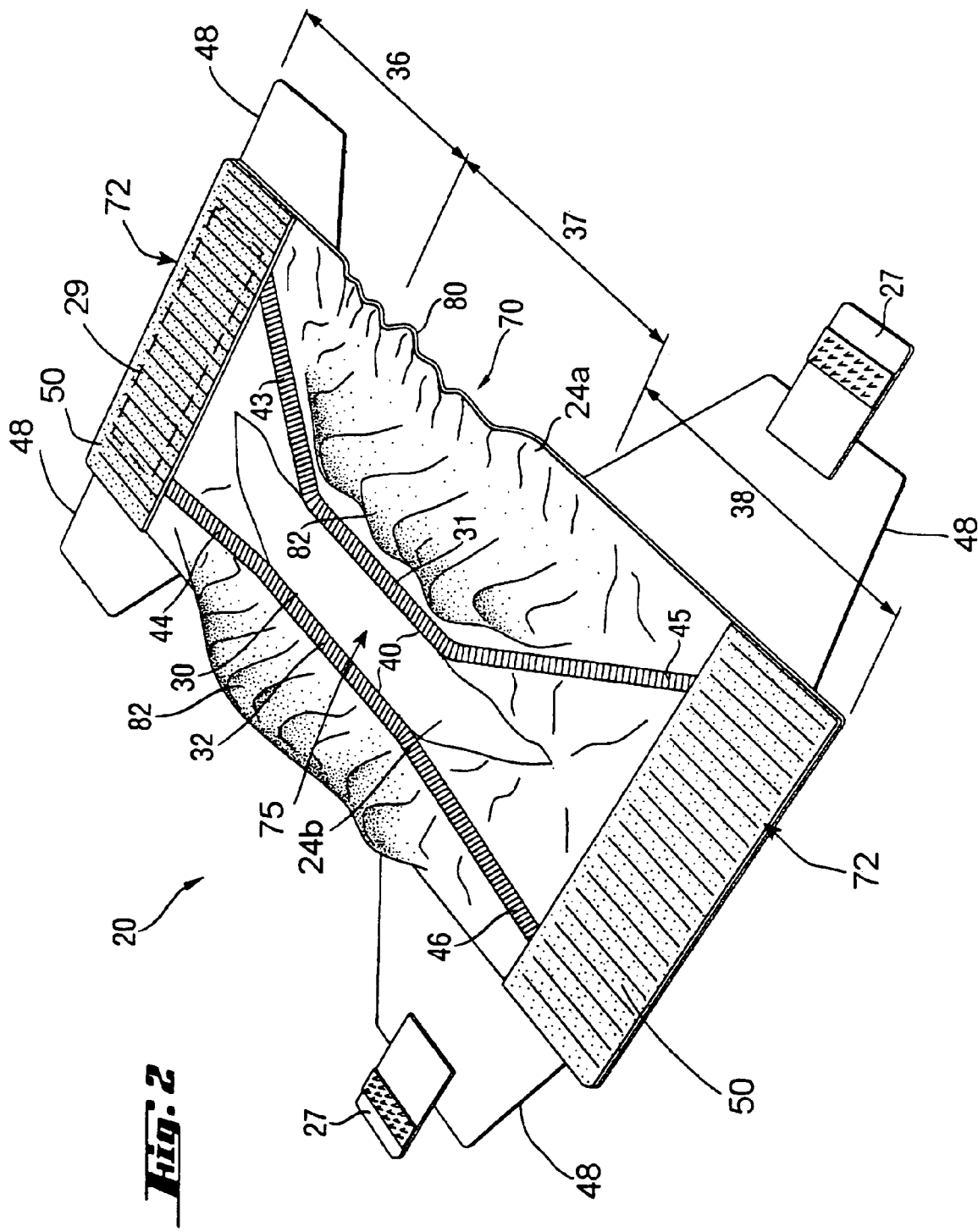
FIG. 2 is a perspective view of the diaper, as shown in FIG. 1, containing the slow recovery elastomer.

FIG. 2 shows a perspective view of the diaper 20 of FIG. 1 in a stretched and substantially planar state. The elasticized topsheet 24a may comprise folds 82 which unfold when a low force, such as less than about 1N, is applied to the elasticized topsheet 24a. The folds 82 may allow the elasticized topsheet 24a to extend during wear. For example, when the secondary topsheet 24b, backsheet 26, and core 28 become heavier upon receipt of bodily exudates and start to sag downwards, the folds 82 can straighten thus allowing the elasticized topsheet 24 to extend and remain positioned in close proximity to the wearer's skin. Also, with limited or no attachment of the elasticized topsheet 24a to the core 28, when the core 28 and backsheet 26 are pulled downwards due to the weight of the exudates received by the diaper 20, the elasticized topsheet 24a and the slit opening 30 do not move automatically with the core but remain against the skin of the wearer, or in very close proximity to the wearer. It is believed that, by minimizing or preventing movement, the slit opening 30 will not increase significantly in lateral size; thus, minimizing potential skin contact with fecal matter.

Figure 3A:
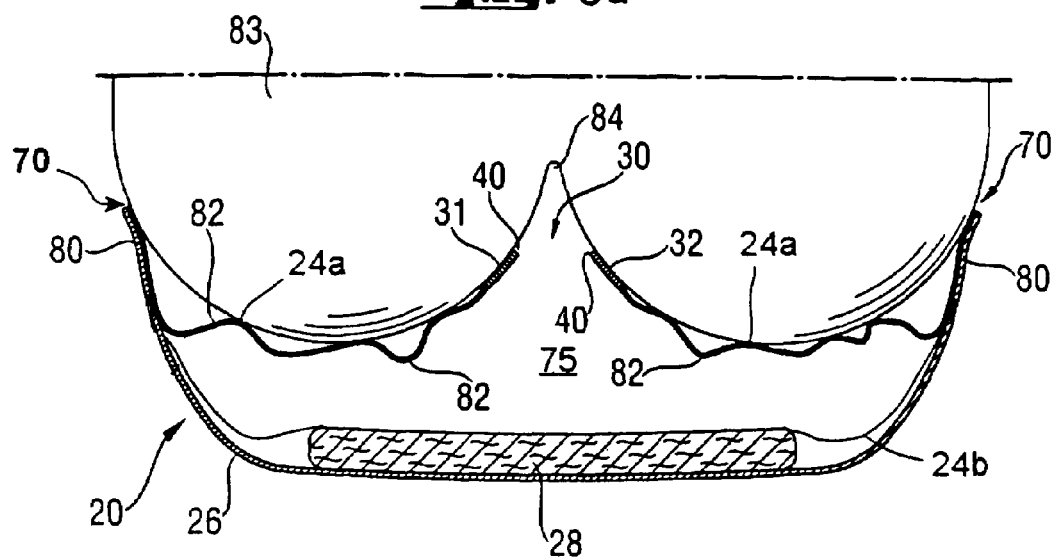
FIGS. 3a and 3b are cross-sectional views of the diaper, as shown in FIGS. 1 and 2, while in use before and after being soiled.
Figure 3B:
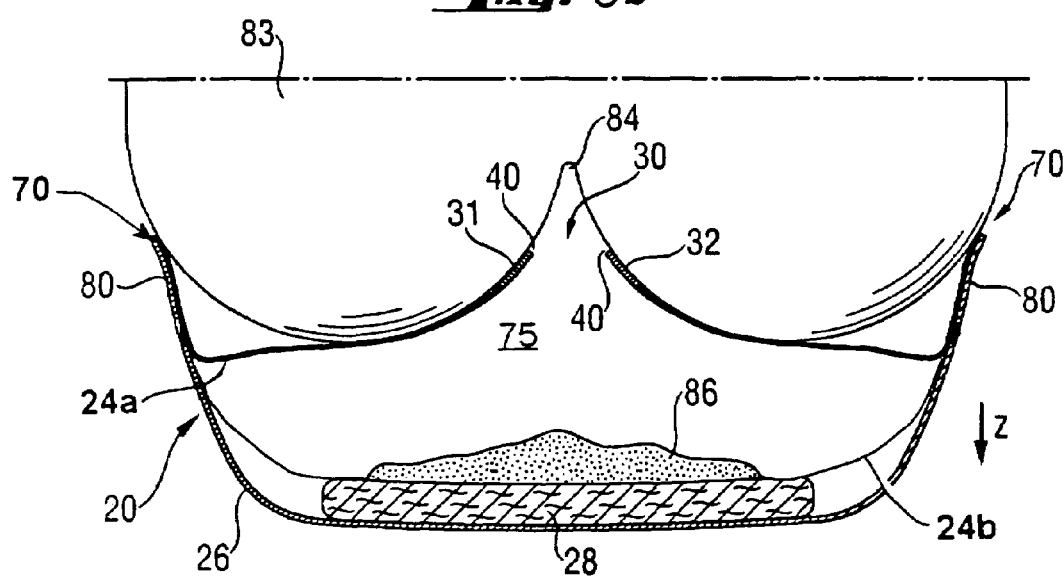

FIGS. 3a-b are cross-sectional views of the diaper 20 taken along a sectional line designated y (i.e., the lateral axis) of FIG. 1. The diaper 20 is being worn by a wearer 83 such that the elasticized topsheet 24a and elastic laminate 31, 32 are in close proximity to the wearer 83. The longitudinal edges 40 are positioned such that the slit opening 30 is positioned along a gluteal groove 84 so as to receive fecal insult. The position of the longitudinal edges 40 and the slit opening 30 may be positioned with respect to the gluteal groove 84 so as to prevent fecal insult on the elasticized topsheet 24a. FIG. 3a shows the diaper prior to receiving exudates. In FIG. 3b, the diaper 20 has received bodily exudates 86. The exudates 86 have passed through the slit opening 30, into the void space 75, and are deposited on the secondary topsheet 24b. The secondary topsheet 24b, core 28, and backsheet 26 now having this increased load may move downward in the z direction (i.e., exhibit sagging). However, the elastic laminates 31, 32 and the slit opening 32 have not moved substantially from the original position shown in FIG. 3a. The folds present in the elasticized topsheet 24a unfurl (i.e., straighten out or unfold) and compensate for the extension of the backsheet 26, core 28, and secondary topsheet 24b in the downward direction.

In other embodiments, the elasticized topsheet 24a and the secondary topsheet 24b may both comprise the elastic laminate of the present invention. In other embodiments, the diaper 20 may take a variety of other forms and constructions as exemplified in U.S. patant application Ser. No. 10/764,939 (U.S. Publication No. US 2004/0193134 A1) entitled "Articles with Cuffs" and filed on Jan. 26, 2004 to Joerg Mueller et al.; U.S. Pat. No. 6,482,191 to Roe et al.; U.S. patent application Ser. No. 10/764,850 (U.S. Publication No. US 2004/0162538 A1) entitled "Articles with Elasticated Topsheets" filed on Jan. 26, 2004 to Joerg Mueller et al.; and U.S. patent application Ser. No. 10/703,239 (U.S. Publication No. US 2004/0092902 A1) entitled "Disposable Absorbent Articles With Masking Topsheet" filed on Nov. 7, 2003 to Anja Hoffmann et al.; U.S. patent application Ser. No. 10/703,233 (U.S. Publication No. US 2004/0092900 A1) entitled "Disposable Absorbent Article With Improved Topsheet" and filed on Nov. 7, 2003 to Anja Hoffmann et al. The slow recovery elastomer of the present invention may be substituted for the elastic regions, bands, or member as disclosed in the referenced application.

The backsheet 26 is generally that portion of the diaper 20 positioned adjacent to the garment facing surface of the absorbent core 28 which prevents the exudates absorbed and contained therein from soiling articles which may contact the diaper 20, such as bedsheets and undergarments. In certain embodiments, the backsheet 26 is impervious to liquids (e.g., urine) and comprises a thin plastic film such as a thermoplastic film having a thickness of about 0.012 mm (0.5 mil) to about 0.051 mm (2.0 mils). Suitable backsheet films include those manufactured by Tredegar Corporation, Richmond, Va., and sold under the trade name CPC2 film. Other suitable backsheet materials may include breathable materials which permit vapors to escape from the diaper 20 while still preventing exudates from passing through the backsheet 26. Exemplary breathable materials may include materials such as woven webs, nonwoven webs, composite materials such as film-coated nonwoven webs, microporous films such as manufactured by Mitsui Toatsu Co., of Japan under the designation ESPOIR NO and by Tredegar Corporation of Richmond, Va. and sold under the designation EXAIRE., and monolithic films such as manufactured by Clopay Corporation, Cincinnati, Ohio under the name HYTREL blend P18-3097. Some breathable composite materials are described in greater detail in PCT Application No. WO 95/16746; U.S. Pat. Nos. 5,938,648; 5,865,823; and 5,571,096.

The backsheet 26, or any portion thereof, may be elastically extensible in one or more directions. In one embodiment, the backsheet 26 may comprise a structural elastic-like film ("SELF") web as described in more detail in U.S. Pat. No. 5,518,801. In other embodiments, the backsheet 26 may comprise elastomeric films, foams, strands, or combinations of these or other suitable materials with nonwovens or synthetic films.

The backsheet 26 may be joined to the topsheets 24a and 24b, the absorbent core 28 and/or any other element of the diaper 20 by any attachment means known in the art. For example, the attachment means may include a uniform continuous layer of adhesive, a patterned layer of adhesive, or an array of separate lines, spirals, or spots of adhesive. One preferred attachment means comprises an open pattern network of filaments of adhesive as disclosed in U.S. Pat. No. 4,573,986. Other suitable attachment means include several lines of adhesive filaments which are swirled into a spiral pattern, as is illustrated by the apparatus and methods shown in U.S. Pat. Nos. 3,911,173; 4,785,996; and 4,842,666. Adhesives that have been found to be satisfactory are manufactured by H. B. Fuller Company, St. Paul, Minn., and marketed as HL-1620 and HL-1358-XZP. Alternatively, the attachment means may comprise heat bonds, pressure bonds, ultrasonic bonds, dynamic mechanical bonds, or any other suitable attachment means or combinations of these attachment means as are known in the art.

The absorbent core 28 may comprise any absorbent material which is generally compressible, conformable, non-irritating to the wearer's skin, and capable of absorbing and retaining liquids such as urine and other certain body exudates. The absorbent core 28 may be manufactured in a wide variety of sizes and shapes (e.g., rectangular, hourglass, "T"-shaped, asymmetric, etc.) and may comprise a wide variety of liquid-absorbent materials commonly used in disposable diapers and other absorbent articles such as comminuted wood pulp, which is generally referred to as airfelt. Examples of other suitable absorbent materials include creped cellulose wadding; meltblown polymers, including coform; chemically stiffened, modified or cross-linked cellulosic fibers; tissue, including tissue wraps and tissue laminates; absorbent foams; absorbent sponges; superabsorbent polymers; absorbent gelling materials; or any other known absorbent material or combinations of materials.

The configuration and construction of the absorbent core 28 may also be varied (e.g., the absorbent core(s) or other absorbent structure(s) may have varying caliper zones, hydrophilic gradient(s), a superabsorbent gradient(s), or lower average density and lower average basis weight acquisition zones; or may comprise one or more layers or structures). Exemplary absorbent structures for use as the absorbent core 28 are described in U.S. Pat. Nos. 4,610,678; 4,673,402; 4,834,735; 4,888,231; 5,137,537; 5,147,345; 5,342,338; 5,260,345; 5,387,207; and 5,625,222.

The diaper 20 may include a fastening system. The fastening system preferably maintains the first waist region 36 and the second waist region 38 in a configuration so as to provide lateral tensions about the circumference of the diaper 20 to hold the diaper 20 on the wearer. The fastening system typically includes at least one engaging component and at least one receiving component. An exemplary fastening system comprises fastening tabs 27 that may be secured to a landing zone 29. Other exemplary fastening systems include, but are not limited to, tape tabs, hook and loop fastening components, interlocking fasteners such as tabs and slots, buckles, buttons, snaps, adhesives, cohesives, and/or hermaphroditic fastening components, although other known fastening means are generally acceptable. Other exemplary surface fastening systems are disclosed in U.S. Pat. Nos. 3,848,594; 4,662,875; 4,846,815; 4,894,060; 4,946,527; 5,151,092; and 5,221,274. An exemplary interlocking fastening system is disclosed in U.S. Pat. No. 6,432,098 entitled "Absorbent Article Fastening Device." The fastening system may also provide a means for holding the article in a disposal configuration as disclosed in U.S. Pat. No. 4,963,140. The fastening system may also include primary and secondary fastening systems, as disclosed in U.S. Pat. No. 4,699,622. The fastening system may also reduce shifting of overlapped portions or improve fit as disclosed in U.S. Pat. Nos. 5,242,436; 5,499,978; 5,507,736; and 5,591,152.

The diaper 20 may include leg cuffs 80 along the longitudinal edges 70 of the diaper 20 and typically attached to the backsheet 26. Leg cuffs 80 may also be referred to as leg bands, side flaps, barrier cuffs, or elastic cuffs. Furthermore, the diaper may include one or more first cuffs which provide improved containment of liquids and other body exudates. First cuffs may also be referred to as outer leg cuff, leg bands, side flaps, leg cuffs or elastic cuffs. Additionally, the diaper may include one or more barrier cuffs which also provide improved containment of liquids and other body exudates. Barrier cuffs may also be referred to as second cuffs, inner leg cuffs or "stand-up" elasticized flaps. U.S. Pat. Nos. 4,695,278 and 4,795,454 issued describe disposable diapers having dual cuffs, including first cuff and second cuff.

Figure 4:
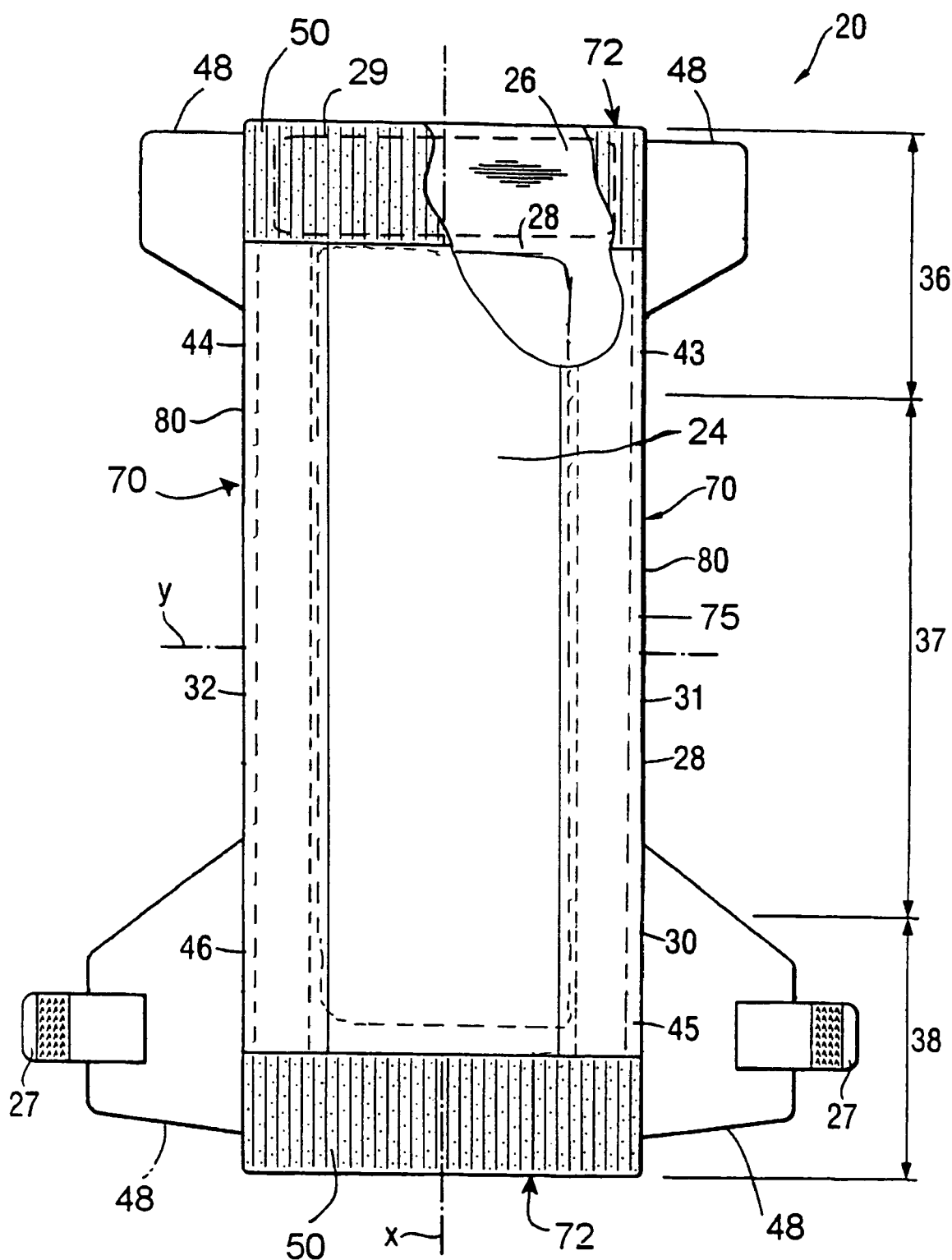
FIG. 4 is a top plan view of another embodiment of a diaper containing the slow recovery elastomer.

FIG. 4 illustrates a diaper 20 in a top plan view, stretched, and in a substantially planar state. The surface of the diaper 20 that is positioned proximate to the wearer (i.e., wearer-facing surface) is shown. Portions of the diaper 20 have been cut away to more clearly show the underlying structure. The diaper 20 of FIG. 4 is configured with a single topsheet 24 and has two pairs of leg cuffs, a pair of gasketing cuffs and a pair of barrier cuffs.

The gasketing cuff 82 may be substantially inelastic or may be elastically extensible to dynamically fit at the wearer's leg. The gasketing cuff 82 may be formed by one or more elastic members 83 operatively joined to the topsheet 24, backsheet 26, or any other suitable substrate used in the formation of the diaper 20. In one suitable embodiment, the gasketing cuff 82 has a plurality of elastic member 83 joined between the backsheet 26 and the topsheet 24. The elastic member 83 may be an elastic material that provides elasticity to the gasketing cuff 82 and may include the slow recovery elastomer of the present invention.

The barrier cuff 84 may be formed by a flap 85 and an elastic member 86. The flap 85 may be a continuous extension of any of the existing materials or elements that form diaper 20. For example, flap 85 may be a portion of the topsheet 24 treated to be hydrophobic or the flap 85 may be a discrete element separately attached to diaper 20. The elastic member 86 may be an elastic material that provides elasticity to the barrier cuff 84 and may include the slow recovery elastomer of the present invention. It is desirable that elastic member 86 exhibits sufficient elasticity such that the barrier cuff may remain in contact with the wearer during normal wear thus enhancing the barrier properties of the barrier cuff 84. U.S. Pat. Nos. 4,808,178 and 4,909,803 describe disposable diapers having barrier cuffs that improve the containment at the leg regions.

The leg cuffs 80 may be treated, in full or in part, with a lotion, as described above. The leg cuffs may further be constructed in a number of different configurations, including those described in U.S. Pat. Nos. 4,636,207; 4,704,115; 4,900,317; 5,085,654; 5,492,751; 6,476,288; and SIR H1630. Any of the leg cuffs disclosed herein as well as other absorbent article components may also be fully or partially coated with a hydrophobic surface coating as detailed in U.S. application Ser. No. 11/055,743, which was filed Feb. 10, 2005.

In some embodiments, such as shown in FIGS. 1 and 4, the diaper 20 may also comprise side panels 48. The side panels 48 may be elastic or extensible to provide a more comfortable and contouring fit by initially conformably fitting the diaper 20 to the wearer and sustaining this fit throughout the time of wear well past when the diaper 20 has been loaded with exudates since the elasticized side panels 48 allow the sides of the diaper 20 to expand and contract. Exemplary construction and configuration of side panels 48 are disclosed in U.S. Pat. Nos. 3,860,003; 4,857,067; 4,381,781; 4,938,753; 5,151,092; 5,221,274; 5,669,897; and 6,004,306.

The diaper 20 may also comprise at least one elastic waist feature 50 that helps to provide improved fit and containment. The elastic waist feature 50 is generally intended to elastically expand and contract to dynamically fit the wearer's waist. The diaper may have two elastic waist features 50, one positioned in the first waist region 36 and one positioned in the second waist region 38. The elastic waist feature 50 may be constructed in a number of different configurations including those described in U.S. Pat. Nos. 4,515,595; 4,710,189; 5,151,092; and 5,221,274. Other suitable waist configurations may include waistcap features such as those described in U.S. Pat. Nos. 5,026,364 and 4,816,025. Elasticity may be provided to the elastic waist feature by inclusion of the slow recovery elastomeric of the present invention.

Some embodiments may also include pockets for receiving and containing waste, spacers which provide voids for waste, barriers for limiting the movement of waste in the article, compartments or voids which accept and contain waste materials deposited in the diaper 20, and the like, or any combinations thereof. Examples of pockets and spacers for use in absorbent products are described in U.S. Pat. Nos. 5,514,121;

5,171,236; 5,397,318; 5,540,671; 6,168,584; 5,306,266; and 5,997,520. Examples of compartments or voids are disclosed in U.S. Pat. Nos. 4,968,312; 4,990,147; 5,062,840; and 5,269,755. Examples of suitable transverse barriers are described in U.S. Pat. No. 5,554,142; WO 94/14395; and U.S. Pat. No. 5,653,703. Examples of other structures especially suitable for management of low viscosity feces are disclosed in U.S. Pat. Nos. 5,941,864; 5,977,430; and 6,013,063.

Figure 5A:
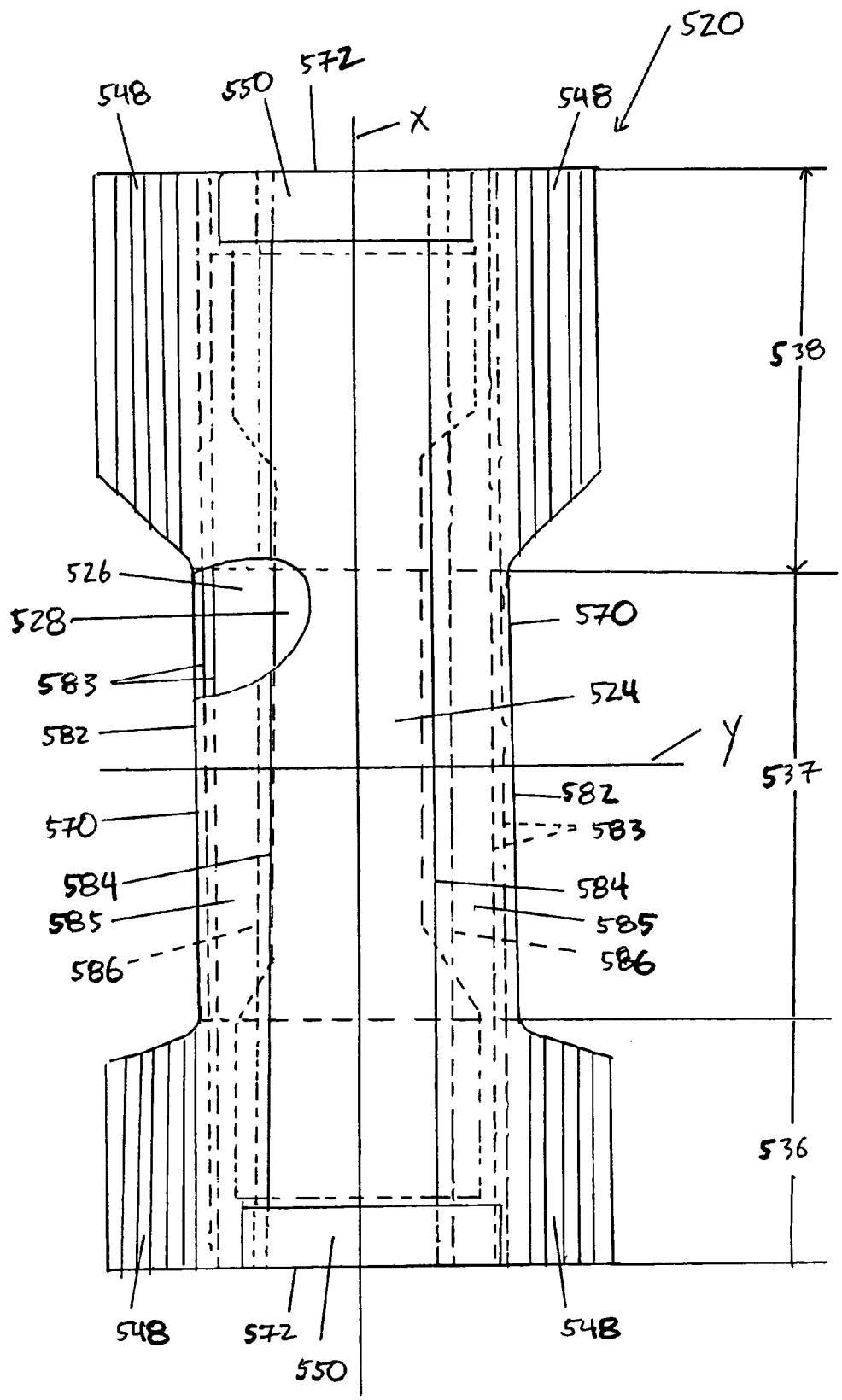
FIG. 5a is a top plan view of another embodiment of the absorbent article as a pant in an unseamed state.
Figure 5B:
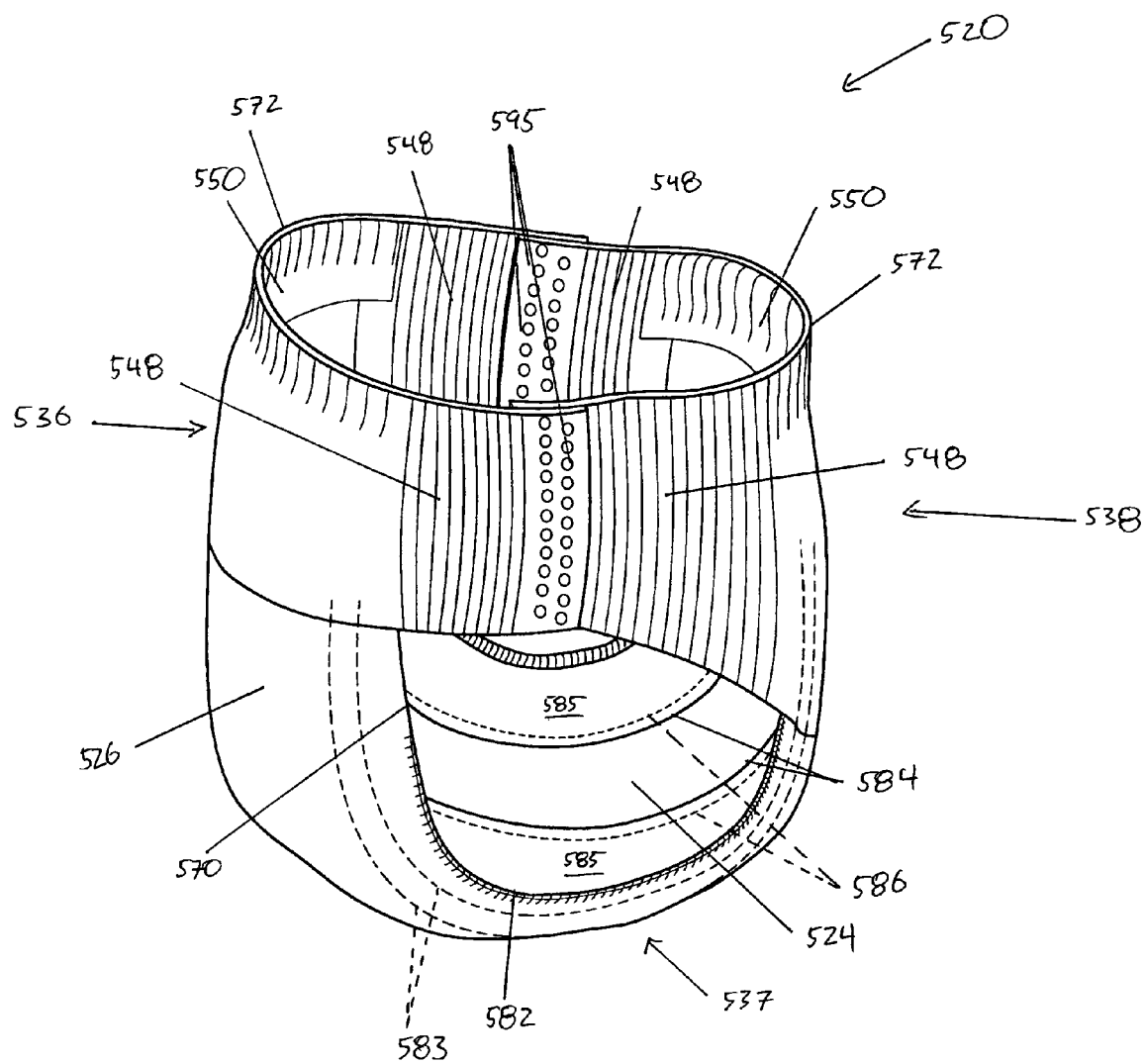
FIG. 5b is a perspective view of the pant of FIG. 5a shown in a seamed state.

In alternative embodiments, the diaper may be pre-formed by the manufacturer to create a pant. Pant generically refers to disposable garments having a waist opening and leg openings designed for infant or adult wearers. Pants are also commonly referred to as "closed diapers," "prefastened diapers," "pull-on diapers," "training pants," and "diaper-pants." The pant may be placed in position on the wearer by inserting the wearer's legs into the leg openings and sliding the pant into position about the wearer's lower torso. An exemplary pant 520 is shown in FIGS. 5a-b. The pant 520 is in a planar unseamed state in FIG. 5a with the wearer-facing surface facing the viewer and is shown seamed in the perspective view of FIG. 5b. The pant 520 has many of the same elements as the diapers of FIGS. 1-4. One end portion of the pant 520 may be configured as a first waist region 536. The opposite end portion may be configured as a second waist region 538. An intermediate portion of the pant 520 may be configured as a crotch region 37 that extends longitudinally between the first and second waist regions 536 and 538.

The pant 520 may comprise two longitudinal edges 570 and two lateral edges 572. The pant 520 may also have a longitudinal axis designated as line x. The diaper may also have a lateral axis designated as line y. The pant 520 may comprise at least one topsheet 524 that may be partially, fully, or not elasticated; a backsheet 526; and an absorbent core 528 interposed between the topsheet 524 and the backsheet 526. The pant 520 may also include side panels 548; one or more pairs of leg cuffs such as gasketing cuffs 582 which may have an elastic member 583 and barrier cuffs 584 which may have a flap 585 and an elastic member 586; and/or a waist feature 550.

The pant may be pre-formed such that the first waist region 536 is joined to the second waist region 538 thereby forming a waist opening and a pair of leg openings. The pant 520 may be pre-formed by having opposing side panels 548 in the first waist region 536 joined to the opposing side panels 548 in the second waist region 538 by a seam 595, as shown in FIG. 5b. The seam 595 may be formed by any suitable bonding means known in the art which is appropriate for the specific materials employed. For example, suitable bonding means may include ultrasonic sealing, heat sealing, pressure bonding, adhesive bonding, sewing, autogenous bonding, and the like. The seams 595 may be permanent, that is, they may be bonded such that separation of the joined opposing side edges 548 requires the rupture or other destructive manipulation of the bonded materials that prevents refastening of the side edges 548. Alternatively, the seam 595 may be refastenable such that it can be opened and refastened repeatedly. Refastenable seams may include hook and loop fasteners and the like. Suitable pants are disclosed in U.S. Pat. Nos. 5,246,433; 5,569,234; 6,120,487; 6,120,489; 4,940,464; 5,092,861; 5,897,545; 5,957,908; and U.S. patent application Ser. No. 10/171,249.

Another embodiment of the present invention is directed toward a method of applying any of the absorbent articles as disclosed above. The absorbent article may be provided to a caregiver for application onto a wearer. The absorbent article may be in a compacted state such that an elastic laminate comprising a slow recovery elastomer is in a relaxed, substantially untensioned state. The caregiver may stretch the absorbent article thereby expanding and tensioning the elastic laminate. The article is generally stretched in preparation for application. The absorbent article can maintain a functionally elongated state for an effective period of time. In one embodiment, the article may maintain an elongated state for a sufficient amount of time necessary for the caregiver to apply the article to the wearer. Upon release of the diaper after stretching, the diaper often contracts and/or folds before it can be successfully applied to a wearer. In one embodiment, slow recovery elastomer exhibits a post elongation strain of at least about 50% after 15 seconds of recovery at 22° C. and an initial strain of 400%. After application, the article may continue to contract so as to provide a snug, ideal fit. This method may be repeated upon soiling of the article during wear.

In another embodiment, a plurality of absorbent articles as disclosed above may be packaged in a kit. Generally, the kit allows for a quantity of absorbent articles to be delivered to and purchased by a consumer while economizing space and simplifying transport and storage. The kit may require activation so that the article becomes accessible (e.g., opening of a lid, removal of a panel, etc.). In one embodiment, the kit is defined by numerous absorbent articles bound together as an entity and covered by a thermoplastic film overwrap as disclosed in U.S. Pat. No. 5,934,470. The thermoplastic film cover may contain an opening means to allow removal of a portion of the thermoplastic film cover and access to the articles. A typical opening means may include a substantially continuous line of weakness, preferably perforations within the thermoplastic film cover. An exemplary opening means is presented in U.S. Pat. No. 5,036,978.

While one kit embodiment is described above, other variations to the kit are clearly envisioned. The overwrap may comprise a variety of materials including, but not limited to, thermoplastic films, nonwovens, wovens, foils, fabrics, papers, cardboard, elastics, cords, straps, and combinations thereof. The overwrap may completely or partially bind and/or cover the plurality of pull-on garments. Other particularly preferred packages and methods for packaging are disclosed in U.S. Pat. Nos. 5,050,742 and 5,054,619. Furthermore, a kit may contain multiple overwraps. For example, a plurality of pull-on garments of the present inventions may be packaged with a thermoplastic film overwrap and then a plurality of film wrapped pull-on garments being overwrapped in a cardboard box or a second thermoplastic film overwrap. Furthermore, the kit may not contain a dedicated opening means. For example, a thermoplastic film overwrap without perforation may simply be opened by tearing the film.

Test Methods

Post Elongation Recovery

This method is used to determine the post elongation strain of an elastomer as a function of temperature and time. The measurement is done at 22° C. (72° F.) or at 32° C. (90° F.). The measurement at 22° C. (72° F.) is designed to simulate the recovery of the elastomer at room temperature, while the measurement at 32° C. (90° F.) is designed to measure the recovery of the elastomer near skin temperature. A two-step analysis, Stretch and Recovery, is performed on the samples. The method employs a Dynamic Mechanical Analyzer (DMA) such as a TA Instruments DMA 2980 (hereinafter "DMA 2980"), available from TA Instruments, Inc., of New Castle, Del.; equipped with a film clamp, Thermal Advantage/Thermal Solutions software for data acquisition, and Universal Analysis 2000 software for data analysis. Many other types of DMA devices exist, and the use of dynamic mechanical analysis is well known to those skilled in the art of polymer and copolymer characterization.

Methods of operation, calibration and guidelines for using the DMA 2980 are found in TA Instruments DMA 2980 Operator's Manual issued March 2002, Thermal Advantage User's Reference Guide issued July 2000 and Universal Analysis 2000 guide issued February 2003. To those skilled in the use of the DMA 2980, the following operational run conditions should be sufficient to replicate the stretch and recovery of the samples.

The experimental conditions are selected on the DMA 2980 which specify operation in the Controlled Force Mode with the film clamp. The film clamp is mounted onto the DMA 2980 and calibrated according to the User's Reference Guide. The material to be tested is cut into samples of substantially uniform dimension. Appropriate sample dimensions may be selected to achieve the required strain. For the DMA 2980, suitable sample dimensions are approximately 6.4 mm wide by approximately 0.15 mm thick. The floating film clamp of the DMA 2980 is adjusted to a position which provides approximately 6 mm between the clamping surfaces, and is locked in this position. The sample is mounted in the film clamps and the lower clamp is allowed to float to allow determination of the actual gauge length which exists between the film clamps. The sample ID and dimensions are recorded. The furnace is closed.

Stretch Method—Specific DMA 2980 parameter settings for the above sample dimensions are set as follows: Preload force applied to sample in clamp (0.01N); auto zero displacement (on) at the start of the test; furnace (close), clamp position (lock), and temperature held at $T_i$ (22° C. or 32° C.) at the end of the stretch method. Data acquisition rate is set at 0.5 Hz (1 point per 2 seconds). The stretch method is loaded onto the DMA 2980. The method segments are (1) Initial Temperature $T_i$ (22° C. or 32° C.), (2) Equilibrate at $T_i$ (3) Data Storage ON, and (4) Ramp Force 5.0 N/min to 18.0 N.

Upon initiation of the test, the temperature ramps to the specified $T_i$ (22° C. or 32° C.) [method segment 1], and the temperature is maintained at this $T_i$ [method segment 2]. After a minimum of 15 minutes at $T_i$, the operator initiates the sample stretching and concurrent data collection [method segments 3 and 4]. The sample is stretched with an applied ramp force of 5 N per minute to approximately 30 mm in length. The gradual increase in force more closely simulates application of the article and prevents breakage. The sample is locked in place at the stretched length of approximately 30 mm and maintained at $T_i$. The force required to reach the 400% strain is recorded manually from the digital readout on the instrument.

For samples of different dimensions, the applied force is adjusted to achieve an applied ramp force of 5 N/min per square millimeter of initial sample cross-sectional area; and the maximum displacement is adjusted to achieve a strain of 400%. The percent strain is calculated by subtracting the gauge length from the stretched length, then dividing the result by the gauge length and multiplying by 100. A sample stretched from an initial length of 6 mm to a length of 30 mm results in a 400% strain.

Recovery Method—The Recovery Method is loaded onto the instrument and initiated 15 seconds after reaching the desired strain (400%) in the Stretch Method. The four segments of the recovery method are (1) Data Storage ON, (2) Force 0.01N, (3) Ramp to $T_i$, and (4) Isotherm for 3.0 minutes. The following DMA 2980 parameter setting is changed from the Stretch Method: auto zero displacement is changed to (OFF). The Recovery Method measures the length of the sample over a 3 minute time period at the specified temperature ($T_i$=either 22° C. or 32° C.). The sample length, percent strain, and test temperature are recorded as a function of recovery time. The post elongation strain is reported as percent strain after different times of recovery (15 seconds, 30 seconds, 60 seconds, and 3 minutes).

For different sample dimensions, the force is adjusted to achieve 0.01 N per square millimeter of initial sample cross-sectional area (determined prior to stretching the sample).

Two Cycle Hysteresis Test

This method is used to determine properties that may correlate with the forces experienced by the consumer during application of the product containing the elastomeric composition and how the product fits and performs once it is applied.

The two cycle hysteresis test method is performed at room temperature (21° C./70° F.) and also at body temperature (37° C./99° F.). The material to be tested is cut into a substantially rectilinear shape. Sample dimensions should be selected to achieve the required strain with forces appropriate for the instrument. Suitable instruments for this test include tensile testers commercially available from MTS Systems Corp., Eden Prairie, Minn. (e.g Alliance RT/1 or Sintech 1/S) or from Instron Engineering Corp., Canton, Mass. For either the Alliance RT/1 or Sintech 1/S instruments listed above, suitable sample dimensions are approximately 0.13 mm thick, approximately 20 mm wide by approximately 100 mm long.

The following procedure illustrates the measurement when using the above sample dimensions and either an Alliance RT/1 or Sintech 1/S. The instrument is interfaced with a computer. TestWorks 4™ software controls the testing parameters, performs data acquisition and calculation, and provides graphs and data reports.

The grips used for the test are wider than the sample. Typically 1" (2.54 cm) wide grips are used. The grips are air actuated grips designed to concentrate the entire gripping force along a single line perpendicular to the direction of testing stress having one flat surface and an opposing face from which protrudes a half round (radius=6 mm) to minimize slippage of the sample. In the case of the measurement at 37° C., the upper grip is a lightweight grip with serrated faces.

The load cell is selected so that the forces measured will be between 10% and 90% of the capacity of the load cell or the load range used. Typically a 25 N load cell is used. The fixtures and grips are installed. The instrument is calibrated according to the manufacturer's instructions. The distance between the lines of gripping force (gauge length) is 2.50" (63.5 mm), which is measured with a steel ruler held beside the grips. The load reading on the instrument is zeroed to account for the mass of the fixture and grips. The mass and thickness of the specimen are measured before testing. The specimen is mounted into the grips in a manner such that there is no slack and the load measured is between 0.00N and 0.02N. After being mounted in the grips, the sample is equilibrated at the testing temperature for 5 minutes before starting the test. A suitable environmental chamber is used to maintain the temp at 37° C. for measurements performed at this temperature. The instrument is located in a temperature-controlled room for measurements performed at 21° C.

The two cycle hysteresis test method involves the following steps:
(1) Strain the sample to the specified maximum percent strain (i.e., $Strain_{max}$=150%) at a constant crosshead speed of 20"/min. (50.8 cm/min) with no hold.
(2) Reduce strain to 0% strain (i.e., return grips to original gauge length of 2.50") at a constant crosshead speed of 3"/min. (7.62 cm/min) with no hold.

(3) Strain the sample to Strain$_{max}$ at a constant crosshead speed of 20"/min. (50.8 cm/min) with no hold.
(4) Reduce strain to 60% strain at a constant crosshead speed of 3"/min. (7.62 cm/min)
(5) Hold at 60% strain for 5 minutes.
(6) Go to 0% strain at a constant crosshead speed 3"/min. (7.62 cm/min)

The measured unload force is the force at 60% strain after the 5 minute hold in step 5. This force is normalized to Newtons per square millimeter of initial sample cross-sectional area (determined before the sample is stretched) as follows: Normalized unload force=measured unload force÷[initial sample thickness in mm×initial sample width in mm]

For different sample dimensions, the crosshead speed is adjusted to maintain the appropriate strain rate for each portion of the test. For example; a crosshead speed of 10"/min (25.4 cm/min) would be used in Steps 1 and 3 for a sample gauge length of 1.25" (31.7 mm).

EXAMPLES

Exemplary films are prepared by blending varying amounts of elastomeric polymer, modifying resin and mineral oil as shown in Table 1. The blending is accomplished by extrusion of the mixture (Examples 2 and 3) or by solvent casting the mixture and pressing into a film on a heated Carver Press (Examples 1, 4, 5, 6 and 7). The amount of each component is expressed in weight percent of the elastomeric composition. The examples in Table 1 comprise a triblock elastomeric copolymer, styrene-isoprene-styrene (S-I-S), commercially available under the trade designation Vector 4211 from Dexco Polymers L. P., Houston, Tex. In some examples (Examples 2, 3, 4, 6 and 7), a component of the elastomeric composition is white mineral oil, commercially available under the trade designation Britol® 50T from Crompton Corporation, Petrolia, Pa. Modifying resins suitable for use that are disclosed in the examples in Table 1 are an alicyclic hydrocarbon resin under the trade designation Arkon P140 (Tg of 86° C.), available from Arakawa Chemical Inc., Chicago, Ill., and poly(t-butyl styrene) (Tg of 126° C. and 130° C. for the 14 kDa and 19 kDa resins, respectively), synthesized at Procter & Gamble Company via free radical polymerization of t-butylstyrene monomer available from Aldrich Chemical Company.

TABLE 1

| Elastomeric Composition (Weight %) | | | | | | | |
|---|---|---|---|---|---|---|---|
| | Sample | | | | | | |
| | 1* | 2 | 3 | 4 | 5 | 6 | 7 |
| Vector 4211 (SIS, 29% S) | 100 | 45 | 45 | 49 | 60 | 59 | 45 |
| Poly(t-butyl styrene), 14 kDa | | 45 | | | | | |
| Poly(t-butyl styrene), 19 kDa | | | 45 | | 40 | 39 | 45 |
| Arkon P140 | | | | 49 | | | |
| Mineral Oil, White Britol-50T | | 10 | 10 | 2 | | 2 | 10 |

*Sample 1 is a comparative example whereas Sample 2-7 are embodiments of the present invention.

The weight average molecular weights of the poly(t-butyl-styrene) samples are 14 and 19 kDa as determined by gel permeation chromatography using polystyrene standards in tetrahydrofuran.

Films of the elastomeric compositions in Table 1 are measured according to the Post Elongation Recovery method described in the Test Methods section above. The thickness of the film tested and the force (not normalized for film thickness) in Newtons to strain the sample to 400% strain are shown in Table 2. The post elongation strain is reported at different recovery times (15 seconds, 30 seconds, 60 seconds, and 3 minutes).

TABLE 2

Post Elongation Strains of Films of the Elastomeric Compositions of Table 1

| | Sample | | | | | | |
|---|---|---|---|---|---|---|---|
| | 1 | 2 | 3 | 4 | 5 | 6 | 7 |
| Post Elongation Strain at 22° C. (72° F.) | | | | | | | |
| Film Thickness (mm) | 0.16 | 0.13 | 0.14 | 0.14 | 0.16 | 0.16 | 0.13 |
| % Strain after 15 seconds recovery | 13 | 137 | 178 | 102 | 153 | 104 | 157 |
| % Strain after 30 seconds recovery | 13 | 98 | 141 | 73 | 117 | 71 | 122 |
| % Strain after 60 seconds recovery | 12 | 64 | 105 | 50 | 88 | 44 | 88 |
| % Strain after 3 minutes recovery | 11 | 29 | 59 | 28 | 48 | 19 | 48 |
| Force (N) | 2.5 | 1.0 | 1.3 | 1.1 | 1.7 | 1.1 | 1.2 |
| Post Elongation Strain at 32° C. (90° F.) | | | | | | | |
| Film Thickness (mm) | 0.15 | 0.14 | 0.13 | 0.14 | 0.16 | 0.14 | 0.14 |
| % Strain after 15 seconds recovery | 16 | 43 | 109 | 41 | 58 | 56 | 81 |
| % Strain after 30 seconds recovery | 15 | 24 | 74 | 27 | 37 | 34 | 53 |
| % Strain after 60 seconds recovery | 15 | 13 | 46 | 18 | 23 | 21 | 33 |
| % Strain after 3 minutes recovery | 14 | 7 | 19 | 11 | 11 | 11 | 16 |
| Force (N) | 1.8 | 0.6 | 0.7 | 0.7 | 1.0 | 0.7 | 0.8 |

The normalized unload forces of films of the elastomeric compositions in Table 1 are measured at 21° C. and 37° C. according to the 2-Cycle Hysteresis Test described in the Test Methods Section above. The data are shown in Table 3.

TABLE 3

Normalized Unload Forces (N/mm²) of Films
of the Elastomeric Compositions of Table 1

| | Sample | | | | | | | |
|---|---|---|---|---|---|---|---|---|
| | 1 | 2 | 3 | 4 | 5 | 6 | 7 | 8[1] |
| Normalized Unload Force at 21° C. (70° F.) [N/mm²] | 0.50 | 0.06 | 0.08 | 0.13 | 0.15 | 0.17 | 0.10 | N.A. |
| Normalized Unload Force at 37° C. (99° F.) [N/mm²] | 0.63 | 0.08 | 0.08 | 0.12 | 0.14 | 0.16 | 0.10 | 0.03 |

[1]Sample No. 8 is a comparative example of Findley H2401 adhesive (pressed into a film using a heated Carver Press).

All documents cited in the Detailed Description of the Invention are, in relevant part, incorporated herein by reference; the citation of any document is not to be construed as an admission that it is prior art with respect to the present invention. To the extent that any definition or meaning of a term in this written document conflicts with a definition or meaning of the term in a document incorporated by reference, the definition or meaning assigned to the term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article comprising:
   a) a topsheet;
   b) a backsheet joined with the topsheet;
   c) an absorbent core interposed between the topsheet and backsheet; and
   d) and elastic member comprising a slow recovery elastomer; wherein the slow recovery elastomer exhibits a normalized unload force at 37° C. of greater than about 0.04 N/mm² and a post elongation strain of at least about 50% after 15 seconds of recovery at 22° C.

2. An absorbent article comprising:
   a) an elasticized topsheet;
   b) a secondary topsheet;
   c) a backsheet joined with the secondary topsheet; and
   d) an absorbent core interposed between the backsheet and the secondary topsheet;
      i) wherein the secondary topsheet is positioned between the core and the elasticized topsheet,
      ii) wherein said elasticized topsheet has a slit opening through the elasticized topsheet, the slit opening allowing entry to a void space between the elasticized topsheet and the secondary topsheet, and
   e) a slow recovery elastomer joined to the elasticized topsheet and in proximity to the slit opening
   wherein the slow recovery elastomer exhibits a normalized unload force at 37° C. of greater than about 0.04 N/mm² and a post elongation strain of at least about 50% after 15 seconds of recovery at 22° C.

3. An absorbent article comprising:
   a) a topsheet;
   b) a backsheet;
   c) an absorbent core interposed between the topsheet and backsheet;
   d) a slow recovery elastomer comprising an elastomeric polymer;
   wherein the slow recovery elastomer exhibits a normalized unload force at 37° C. of greater than about 0.04 N/mm² and a post elongation strain of at least about 50% after 15 seconds of recovery at 22° C.

4. The absorbent article of claim 3 wherein the elastomeric polymer is selected from the group consisting of styrenic block copolymers, natural and synthetic rubbers, polyisoprene, neoprene, polyurethanes, silicone rubbers, hydrocarbon elastomers, ionomers, and combinations thereof.

5. The absorbent article of claim 3 wherein the elastomeric polymer is a block copolymer comprising at least one substantially soft block and at least one substantially hard block.

6. The absorbent article of claim 5 wherein the elastomeric polymer is a triblock copolymer comprising a hard/soft/hard block configuration.

7. The absorbent article of claim 6 wherein the elastomeric polymer is a triblock copolymer selected from the group comprising styrene/isoprene/styrene, styrene/butadiene/styrene, and combinations thereof.

8. The absorbent article of claim 3 wherein the slow recovery elastomer comprises from about 0.01% to about 60%, by weight, of a modifying resin.

9. The absorbent article of claim 8 wherein the modifying resin is selected from the group consisting of unhydrogenated C5 hydrocarbon resins or C9 hydrocarbon resins, partially and fully hydrogenated C5 hydrocarbon resins or C9 hydrocarbon resins; cycloaliphatic resins; terpene resins; polystyrene and styrene oligomers; poly(t-butylstyrene) or oligomers thereof; rosin and rosin derivatives; coumarone indenes; polycyclopentadiene and oligomers thereof; polymethylstyrene or oligomers thereof; phenolic resins; indene polymers, oligomers and copolymers; acrylate and methacrylate oligomers, polymers, or copolymers; derivatives thereof; and combinations thereof.

10. The absorbent article of claim 9 wherein the modifying resin is selected from the group consisting of C5 hydrocarbon resins or C9 hydrocarbon resins and hydrogenated derivatives thereof, alicyclic hydrocarbon resin, terpene phenolic resin, poly(t-butylstyrene), poly(iso-bornylmethacrylate), poly(indene-co-coumarone), poly(vinylcyclohexane), terpenes, poly(methylstyrene-co-indene), cycloaliphatic resin, poly-beta-pinene, and poly(3,3,5-trimethylcyclohexyl methacrylate), polycyclopentadiene, polymethyistyrene, derivatives thereof, and combinations thereof.

11. The absorbent article of claim 3 wherein the slow recovery elastomer further comprises an additive selected from the group comprising stabilizers, antioxidants, viscosity modifiers, processing aids, bacteriostats, colorants, fillers, or combinations thereof.

12. The absorbent article of claim 3 wherein the slow recovery elastomer is in a form selected from the group consisting of a film, strand, band, foam, and combinations thereof.

13. The absorbent article of claim 3 wherein at least one topsheet is in the form of an elasticized topsheet.

14. The absorbent article of claim 13 wherein the elasticized topsheet further comprises a slit opening allowing for waste passage.

15. The absorbent article of claim 14 wherein the slow recovery elastomer is joined to the elasticized topsheet and runs substantially longitudinally adjacent to the slit opening.

16. The absorbent article of claim 3 wherein the article portion with the slow recovery elastomer joined thereto comprises a secondary elastomer joined to the article portion, wherein the secondary elastomer exhibits less than about 50% post elongation strain at 22° C. after 15 seconds of recovery.

17. The absorbent article of claim 3 wherein the absorbent article is selected from the group comprising diapers, training pants, pull-on garments, refastenable pants, adult incontinence products, or feminine care products.

18. A kit comprising a first absorbent article as in claim 3 and a second absorbent article as in claim 3, the first absorbent article and the second absorbent article being covered by an overwrap.

19. The absorbent article of claim 3, wherein the slow recovery elastomer exhibits a post elongation strain of at least about 102% after 15 seconds of recovery at 22° C.

20. The absorbent article of claim 19, wherein the slow recovery elastomer exhibits a post elongation strain of at least about 70% after 30 seconds of recovery at 22° C.

21. The absorbent article of claim 19, wherein the slow recovery elastomer exhibits a post elongation strain of at least about 40% after 60 seconds of recovery at 22° C.

22. The absorbent article of claim 19, wherein the slow recovery elastomer exhibits a post elongation strain of at least about 20% after 180 seconds of recovery at 22° C.

23. The absorbent article of claim 19, wherein the slow recovery elastomer exhibits a post elongation strain of at least about 41% after 15 seconds of recovery at 32° C.

24. The absorbent article of claim 19, wherein the slow recovery elastomer exhibits a post elongation strain of at least about 24% after 30 seconds of recovery at 32° C.

25. The absorbent article of claim 19, wherein the slow recovery elastomer exhibits a post elongation strain of at least about 13% after 60 seconds of recovery at 32° C.

26. The absorbent article of claim 19, wherein the slow recovery elastomer exhibits a post elongation strain of at least about 7% after 180 seconds of recovery at 32° C.

27. The absorbent article of claim 3, wherein the slow recovery elastomer exhibits a post elongation strain of from about 75% to about 150% after 15 seconds of recovery at 22° C.

28. The absorbent article of claim 27, wherein the slow recovery elastomer exhibits a post elongation strain of at least about 70% after 30 seconds of recovery at 22° C.

29. The absorbent article of claim 3, wherein the slow recovery elastomer exhibits a post elongation strain of at least about 170% after 15 seconds of recovery at 22° C.

30. The absorbent article of claim 3, wherein the slow recovery elastomer exhibits a post elongation strain of at least about 40% after 60 seconds of recovery at 22° C.

31. The absorbent article of claim 3, wherein the slow recovery elastomer exhibits a post elongation strain of at least about 19% after 180 seconds of recovery at 22° C.

32. The absorbent article of claim 3, wherein the slow recovery elastomer exhibits a post elongation strain of at least about 41% after 15 seconds of recovery at 32° C.

33. The absorbent article of claim 3, wherein the slow recovery elastomer exhibits a post elongation strain of at least about 24% after 30 seconds of recovery at 32° C.

34. The absorbent article of claim 33, wherein the slow recovery elastomer exhibits a post elongation strain of at least about 13% after 60 seconds of recovery at 32° C.

35. The absorbent article of claim 3, wherein the slow recovery elastomer exhibits a post elongation strain of at least about 13% after 60 seconds of recovery at 32° C.

36. The absorbent article of claim 35, wherein the slow recovery elastomer exhibits a post elongation strain of at least about 7% after 180 seconds of recovery at 32° C.

37. The absorbent article of claim 3, wherein the slow recovery elastomer exhibits a post elongation strain of at least about 7% after 180 seconds of recovery at 32° C.

38. The absorbent article of claim 3 wherein the post elongation strain of the slow recovery elastomer after 15 seconds of recovery at 22° C. minus the post elongation strain of the slow recovery elastomer after 15 seconds of recovery at 32° C. is at least about 35%.

39. The absorbent article of claim 3 wherein the post elongation strain of the slow recovery elastomer after 15 seconds of recovery at 22° C. minus the post elongation strain of the slow recovery elastomer after 15 seconds of recovery at 32° C. is at least about 50%.

40. The absorbent article of claim 3 wherein the post elongation strain of the slow recovery elastomer after 15 seconds of recovery at 22° C. minus the post elongation strain of the slow recovery elastomer after 15 seconds of recovery at 32° C. is at least about 75%.

41. The absorbent article of claim 3 wherein the slow recovery elastomer is joined to one or more article portions selected from the group consisting of the topsheet, the backsheet, the core, an anal cuff, an elasticized topsheet, a fastening system, a leg cuff, a waist elastic feature, a side panel, a pocket, a spacer, and combinations thereof.

42. The absorbent article of claim 3 wherein the slow recovery elastomer comprises from about 20% to about 70%, by weight, of the elastomeric polymer.

43. The absorbent article of claim 3 wherein the slow recovery elastomer comprises from about 20% to about 55%, by weight, of a modifying resin.

44. The absorbent article of claim 3 wherein the slow recovery elastomer comprises from about 35% to about 45%, by weight, of a modifying resin.

45. The absorbent article of claim 3 wherein the slow recovery elastomer exhibits a normalized unload force at 37° C. of greater than about 0.08 N/mm$^2$.

46. The absorbent article of claim 3 wherein the slow recovery elastomer exhibits a normalized unload force at 37° C. of greater than about 0.12 N/mm$^2$.

47. The absorbent article of claim 3, wherein the slow recovery elastomer exhibits a post elongation strain of at least about 153% after 15 seconds of recovery at 22° C.

48. The absorbent article of claim 3 wherein the post elongation strain of the slow recovery elastomer after 15 seconds of recovery at 22° C. minus the post elongation strain of the slow recovery elastomer after 15 seconds of recovery at 32° C. is at least about 94%.

49. An absorbent article comprising:
   a) a topsheet;
   b) a backsheet;
   c) an absorbent core interposed between the topsheet and backsheet;

d) a slow recovery elastomer comprising an elastomeric polymer;
wherein the slow recovery elastomer exhibits a normalized unload force at 37° C. of greater than about 0.04 N/mm$^2$; and
wherein a post elongation strain of the slow recovery elastomer after 15 seconds of recovery at 22° C. minus a post elongation strain of the slow recovery elastomer after 15 seconds of recovery at 32° C. is at least about 35%.

50. The absorbent article of claim 49, wherein the slow recovery elastomer exhibits a post elongation strain of at least about 50% after 15 seconds of recovery at 22° C.

51. The absorbent article of claim 50, wherein the slow recovery elastomer exhibits a post elongation strain of at least about 40% after 60 seconds of recovery at 22° C.

52. The absorbent article of claim 50, wherein the slow recovery elastomer exhibits a post elongation strain of at least about 19% after 180 seconds of recovery at 22° C.

53. The absorbent article of claim 50, wherein the slow recovery elastomer exhibits a post elongation strain of at least about 41% after 15 seconds of recovery at 32° C.

54. The absorbent article of claim 50, wherein the slow recovery elastomer exhibits a post elongation strain of at least about 24% after 30 seconds of recovery at 32° C.

55. The absorbent article of claim 50, wherein the slow recovery elastomer exhibits a post elongation strain of at least about 13% after 60 seconds of recovery at 32° C.

56. The absorbent article of claim 50, wherein the slow recovery elastomer exhibits a post elongation strain of at least about 7% after 180 seconds of recovery at 32° C.

57. The absorbent article of claim 49, wherein the slow recovery elastomer exhibits a post elongation strain of at least about 102% after 15 seconds of recovery at 22° C.

58. The absorbent article of claim 57, wherein the slow recovery elastomer exhibits a post elongation strain of at least about 70% after 30 seconds of recovery at 22° C.

59. The absorbent article of claim 57, wherein the slow recovery elastomer exhibits a post elongation strain of at least about 40% after 60 seconds of recovery at 22° C.

60. The absorbent article of claim 57, wherein the slow recovery elastomer exhibits a post elongation strain of at least about 20% after 180 seconds of recovery at 22° C.

61. The absorbent article of claim 57, wherein the slow recovery elastomer exhibits a post elongation strain of at least about 41% after 15 seconds of recovery at 32° C.

62. The absorbent article of claim 57, wherein the slow recovery elastomer exhibits a post elongation strain of at least about 24% after 30 seconds of recovery at 32° C.

63. The absorbent article of claim 57, wherein the slow recovery elastomer exhibits a post elongation strain of at least about 13% after 60 seconds of recovery at 32° C.

64. The absorbent article of claim 57, wherein the slow recovery elastomer exhibits a post elongation strain of at least about 7% after 180 seconds of recovery at 32° C.

65. The absorbent article of claim 49, wherein the slow recovery elastomer exhibits a post elongation strain of from about 75% to about 150% after 15 seconds of recovery at 22° C.

66. The absorbent article of claim 65, wherein the slow recovery elastomer exhibits a post elongation strain of at least about 70% after 30 seconds of recovery at 22° C.

67. The absorbent article of claim 49, wherein the slow recovery elastomer exhibits a post elongation strain of at least about 170% after 15 seconds of recovery at 22° C.

68. The absorbent article of claim 49, wherein the slow recovery elastomer exhibits a post elongation strain of at least about 70% after 30 seconds of recovery at 22° C.

69. The absorbent article of claim 49, wherein the slow recovery elastomer exhibits a post elongation strain of at least about 40% after 60 seconds of recovery at 22° C.

70. The absorbent article of claim 49, wherein the slow recovery elastomer exhibits a post elongation strain of at least about 19% after 180 seconds of recovery at 22° C.

71. The absorbent article of claim 49, wherein the slow recovery elastomer exhibits a post elongation strain of at least about 41% after 15 seconds of recovery at 32° C.

72. The absorbent article of claim 49, wherein the slow recovery elastomer exhibits a post elongation strain of at least about 24% after 30 seconds of recovery at 32° C.

73. The absorbent article of claim 72, wherein the slow recovery elastomer exhibits a post elongation strain of at least about 13% after 60 seconds of recovery at 32° C.

74. The absorbent article of claim 49, wherein the slow recovery elastomer exhibits a post elongation strain of at least about 13% after 60 seconds of recovery at 32° C.

75. The absorbent article of claim 74, wherein the slow recovery elastomer exhibits a post elongation strain of at least about 7% after 180 seconds of recovery at 32° C.

76. The absorbent article of claim 49, wherein the slow recovery elastomer exhibits a post elongation strain of at least about 7% after 180 seconds of recovery at 32° C.

77. The absorbent article of claim 49 wherein the post elongation strain of the slow recovery elastomer after 15 seconds of recovery at 22° C. minus the post elongation strain of the slow recovery elastomer after 15 seconds of recovery at 32° C. is at least about 50%.

78. The absorbent article of claim 49 wherein the post elongation strain of the slow recovery elastomer after 15 seconds of recovery at 22° C. minus the post elongation strain of the slow recovery elastomer after 15 seconds of recovery at 32° C. is at least about 75%.

79. The absorbent article of claim 49 wherein the slow recovery elastomer is joined to one or more article portions selected from the group consisting of the topsheet, the backsheet, the core, an anal cuff, an elasticized topsheet, a fastening system, a leg cuff, a waist elastic feature, a side panel, a pocket, a spacer, and combinations thereof.

80. The absorbent article of claim 49 wherein the slow recovery elastomer comprises from about 20% to about 70%, by weight, of the elastomeric polymer.

81. The absorbent article of claim 49 wherein the slow recovery elastomer comprises from about 20% to about 55%, by weight, of a modifying resin.

82. The absorbent article of claim 49 wherein the slow recovery elastomer comprises from about 35% to about 45%, by weight, of a modifying resin.

83. The absorbent article of claim 49 wherein the slow recovery elastomer exhibits a normalized unload force at 37° C. of greater than about 0.08 N/mm$^2$.

84. The absorbent article of claim 49 wherein the slow recovery elastomer exhibits a normalized unload force at 37° C. of greater than about 0.12 N/mm$^2$.

85. The absorbent article of claim 49 wherein the elastomeric polymer is selected from the group consisting of styrenic block copolymers, natural and synthetic rubbers, polyisoprene, neoprene, polyurethanes, silicone rubbers, hydrocarbon elastomers, ionomers, and combinations thereof.

86. The absorbent article of claim 49 wherein the elastomeric polymer is a block copolymer comprising at least one substantially soft block and at least one substantially hard block.

87. The absorbent article of claim 86 wherein the elastomeric polymer is a triblock copolymer comprising a hard/soft/hard block configuration.

88. The absorbent article of claim 87 wherein the elastomeric polymer is a triblock copolymer selected from the group comprising styrene/isoprene/styrene, styrene/butadiene/styrene, and combinations thereof.

89. The absorbent article of claim 49 wherein the slow recovery elastomer comprises from about 0.01% to about 60%, by weight, of a modifying resin.

90. The absorbent article of claim 89 wherein the modifying resin is selected from the group consisting of unhydrogenated C5 hydrocarbon resins or C9 hydrocarbon resins, partially and fully hydrogenated C5 hydrocarbon resins or C9 hydrocarbon resins; cycloaliphatic resins; terpene resins; polystyrene and styrene oligomers; poly(t-butylstyrene) or oligomers thereof; rosin and rosin derivatives; coumarone indenes; polycyclopentadiene and oligomers thereof; polymethyistyrene or oligomers thereof; phenolic resins; indene polymers, oligomers and copolymers; acrylate and methacrylate oligomers, polymers, or copolymers; derivatives thereof; and combinations thereof.

91. The absorbent article of claim 90 wherein the modifying resin is selected from the group consisting of C5 hydrocarbon resins or C9 hydrocarbon resins and hydrogenated derivatives thereof, alicyclic hydrocarbon resin, terpene phenolic resin, poly(t-butylstyrene), poly(iso-bornylmethacrylate), poly(indene-co-coumarone), poly(vinylcyclohexane), terpenes, poly(methylstyrene-co-indene), cycloaliphatic resin, poly-beta-pinene, and poly(3,3,5-trimethylcyclohexyl methacrylate), polycyclopentadiene, polymethylstyrene, derivatives thereof, and combinations thereof.

92. The absorbent article of claim 49 wherein the slow recovery elastomer further comprises an additive selected from the group comprising stabilizers, antioxidants, viscosity modifiers, processing aids, bacteriostats, colorants, fillers, or combinations thereof.

93. The absorbent article of claim 49 wherein the slow recovery elastomer is in a form selected from the group consisting of a film, strand, band, foam, and combinations thereof.

94. The absorbent article of claim 49 wherein at least one topsheet is in the form of an elasticized topsheet.

95. The absorbent article of claim 94 wherein the elasticized topsheet further comprises a slit opening allowing for waste passage.

96. The absorbent article of claim 95 wherein the slow recovery elastomer is joined to the elasticized topsheet and runs substantially longitudinally adjacent to the slit opening.

97. The absorbent article of claim 49 wherein the article portion with the slow recovery elastomer joined thereto comprises a secondary elastomer joined to the article portion, wherein the secondary elastomer exhibits less than about 50% post elongation strain at 22° C. after 15 seconds of recovery.

98. The absorbent article of claim 49 wherein the absorbent article is selected from the group comprising diapers, training pants, pull-on garments, refastenable pants, adult incontinence products, or feminine care products.

99. A kit comprising a first absorbent article as in claim 49 and a second absorbent article as in claim 49, the first absorbent article and the second absorbent article being covered by an overwrap.

100. The absorbent article of claim 49, wherein the slow recovery elastomer exhibits a post elongation strain of at least about 153% after 15 seconds of recovery at 22° C.

101. The absorbent article of claim 49 wherein the post elongation strain of the slow recovery elastomer after 15 seconds of recovery at 22° C. minus the post elongation strain of the slow recovery elastomer after 15 seconds of recovery at 32° C. is at least about 94%.

* * * * *

UNITED STATES PATENT AND TRADEMARK OFFICE
CERTIFICATE OF CORRECTION

PATENT NO. : 7,717,893 B2  
APPLICATION NO. : 11/144508  
DATED : May 18, 2010  
INVENTOR(S) : Hird et al.

It is certified that error appears in the above-identified patent and that said Letters Patent is hereby corrected as shown below:

Column 24
Line 61, delete "polymethyistyrene" and insert --polymethylstyrene--.

Column 29
Lines 18 and 19, delete "polymethyistyrene" and insert --polymethylstyrene--.

Signed and Sealed this
Twenty-fifth Day of October, 2011

David J. Kappos
*Director of the United States Patent and Trademark Office*